(12) United States Patent
Killen

(10) Patent No.: US 9,601,913 B2
(45) Date of Patent: Mar. 21, 2017

(54) ROLLABLE WIRE DISPENSING SPOOL RACK

(71) Applicant: Crit Randall Killen, Orem, UT (US)

(72) Inventor: Crit Randall Killen, Orem, UT (US)

( * ) Notice: Subject to any disclaimer, the term of this patent is extended or adjusted under 35 U.S.C. 154(b) by 376 days.

(21) Appl. No.: 14/266,494

(22) Filed: Apr. 30, 2014

(65) Prior Publication Data

US 2014/0339353 A1 Nov. 20, 2014

Related U.S. Application Data

(63) Continuation of application No. 13/506,597, filed on Apr. 30, 2012, now abandoned.

(Continued)

(51) Int. Cl.
*B65H 75/40* (2006.01)
*H02G 11/02* (2006.01)
*A61F 2/40* (2006.01)
*A61F 2/30* (2006.01)
*A61F 2/36* (2006.01)
*A61F 2/38* (2006.01)
*A61B 17/72* (2006.01)
*A61B 17/80* (2006.01)

(52) U.S. Cl.
CPC .......... *H02G 11/02* (2013.01); *A61F 2/3662* (2013.01); *A61F 2/3676* (2013.01); *A61F 2/4059* (2013.01); *B65H 75/40* (2013.01); *A61B 17/72* (2013.01); *A61B 17/80* (2013.01); *A61F 2/3094* (2013.01); *A61F 2/3601* (2013.01); *A61F 2/389* (2013.01); *A61F 2/3859* (2013.01); *A61F 2002/30289* (2013.01); *A61F 2002/30566* (2013.01); *A61F 2002/30594* (2013.01); *A61F 2002/30769* (2013.01); *A61F 2002/30822* (2013.01); *A61F 2002/30968* (2013.01); *A61F 2002/3692* (2013.01); *A61F 2002/3694* (2013.01)

(58) Field of Classification Search
CPC ........ B65H 49/00; B65H 49/20; B65H 49/32; B65H 49/325; B65H 49/38; B65H 75/04; B65H 75/14; B65H 75/40; H02G 11/02
See application file for complete search history.

(56) References Cited

U.S. PATENT DOCUMENTS 3,652,026 A * 3/1972 Awebro ................. B65H 49/20
242/403.1
3,856,230 A * 12/1974 Zimmer ................... B62B 1/22
242/422.8

(Continued)

Primary Examiner — William A Rivera
(74) Attorney, Agent, or Firm — Tran & Associates

(57) ABSTRACT

A rollable dispenser for spooled wire includes equiangularly-spaced tubular braces which rigidly interconnect the frames adjacent their circular peripheral edges. One or more wire spools are retained between the platters on removable axles which span the distance between both platters at radial intervals. One or more spools may also be retained by a centrally positioned axle. For a preferred embodiment of the invention, each platter is constructed from a length of circularly-bent tubing, the ends of which are butt welded together to form a hoop. Each platter further includes a circular laminar plate that includes a circular rim, a central hub having a single axle aperture, and radial laminar spokes, each having an axle aperture, which join the rim to the hub.

19 Claims, 19 Drawing Sheets

Swing out brake
in neutral position

Swing out brake
in active position

Related U.S. Application Data

(60) Provisional application No. 61/480,113, filed on Apr. 28, 2011.

(56) References Cited

U.S. PATENT DOCUMENTS

| | | | | |
|---|---|---|---|---|
| 4,391,422 A * | 7/1983 | McDonald | ............... | B62B 1/264 |
| | | | | 242/129.6 |
| 4,605,237 A * | 8/1986 | Torgrimson | ......... | B65H 49/325 |
| | | | | 242/557 |
| 6,948,680 B2 * | 9/2005 | Ganster | ................. | B65D 85/04 |
| | | | | 206/400 |
| 7,044,419 B2 * | 5/2006 | Moore | ................... | B65H 35/00 |
| | | | | 242/559.2 |
| 7,984,870 B2 * | 7/2011 | Gonzales | ............. | B60P 7/0846 |
| | | | | 242/404.1 |
| 8,403,345 B2 * | 3/2013 | Iossa | ...................... | B65H 49/32 |
| | | | | 242/557 |
| 8,616,485 B2 * | 12/2013 | Iossa | ...................... | B65H 49/32 |
| | | | | 242/403 |

* cited by examiner

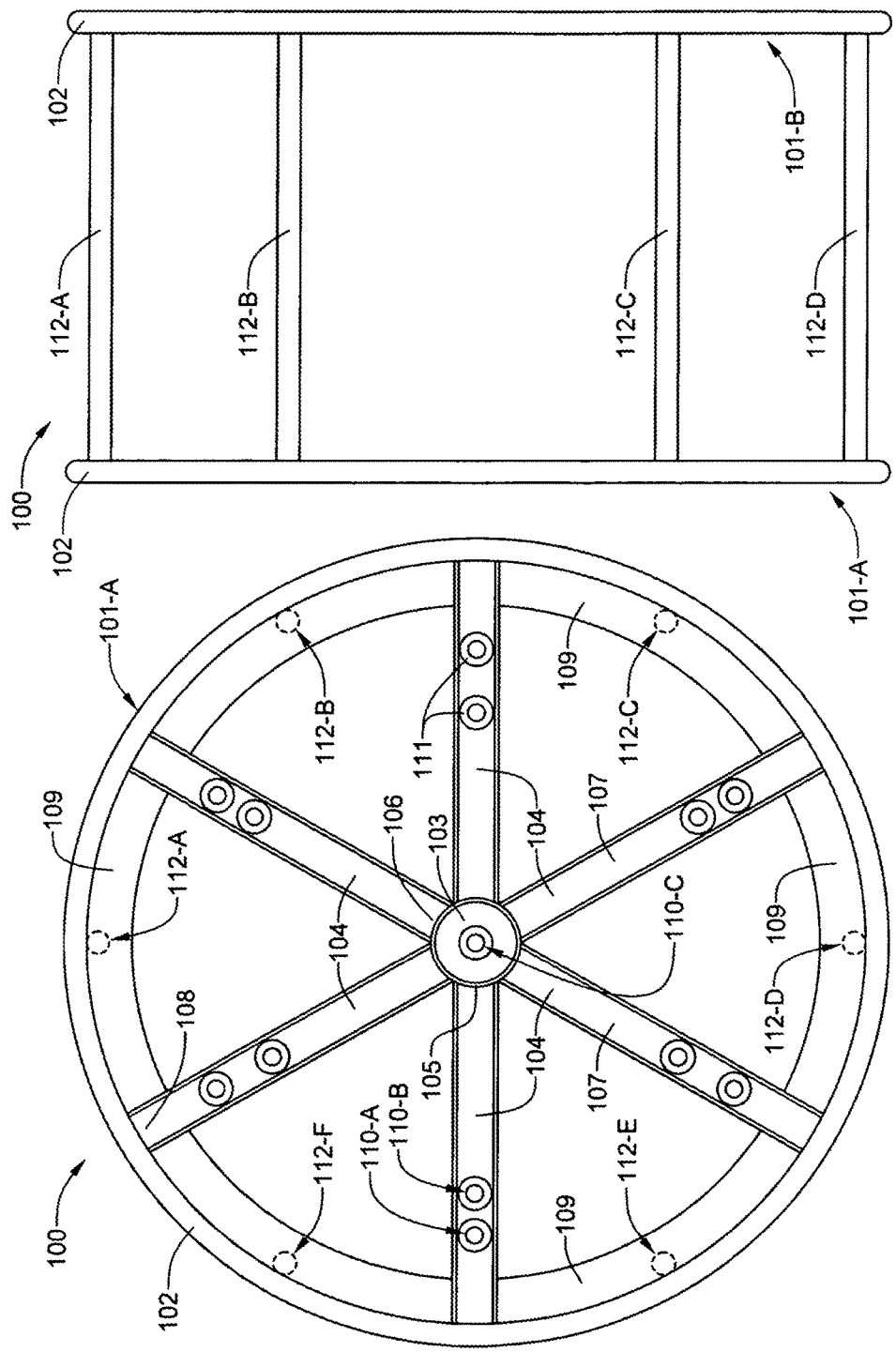

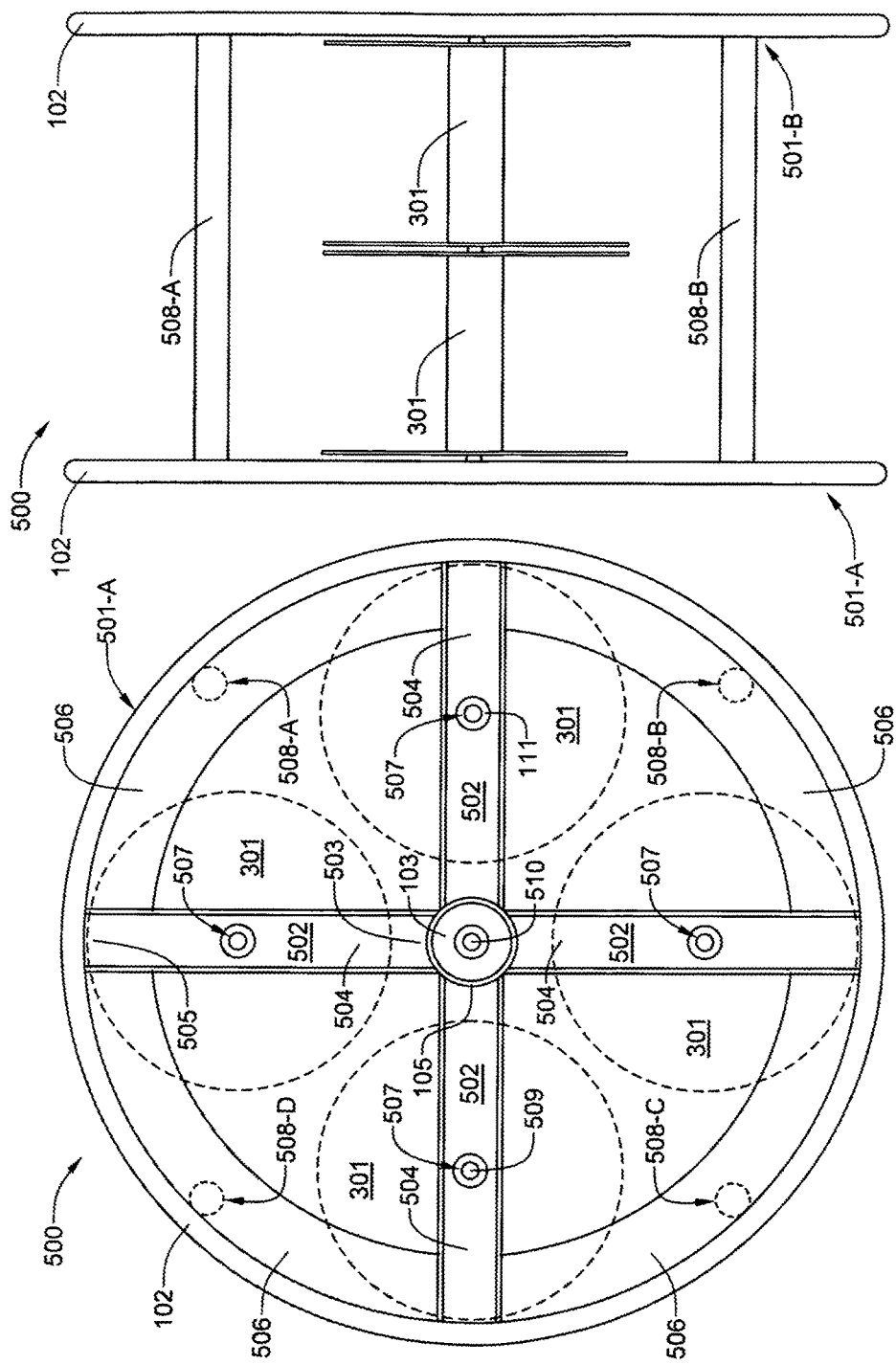

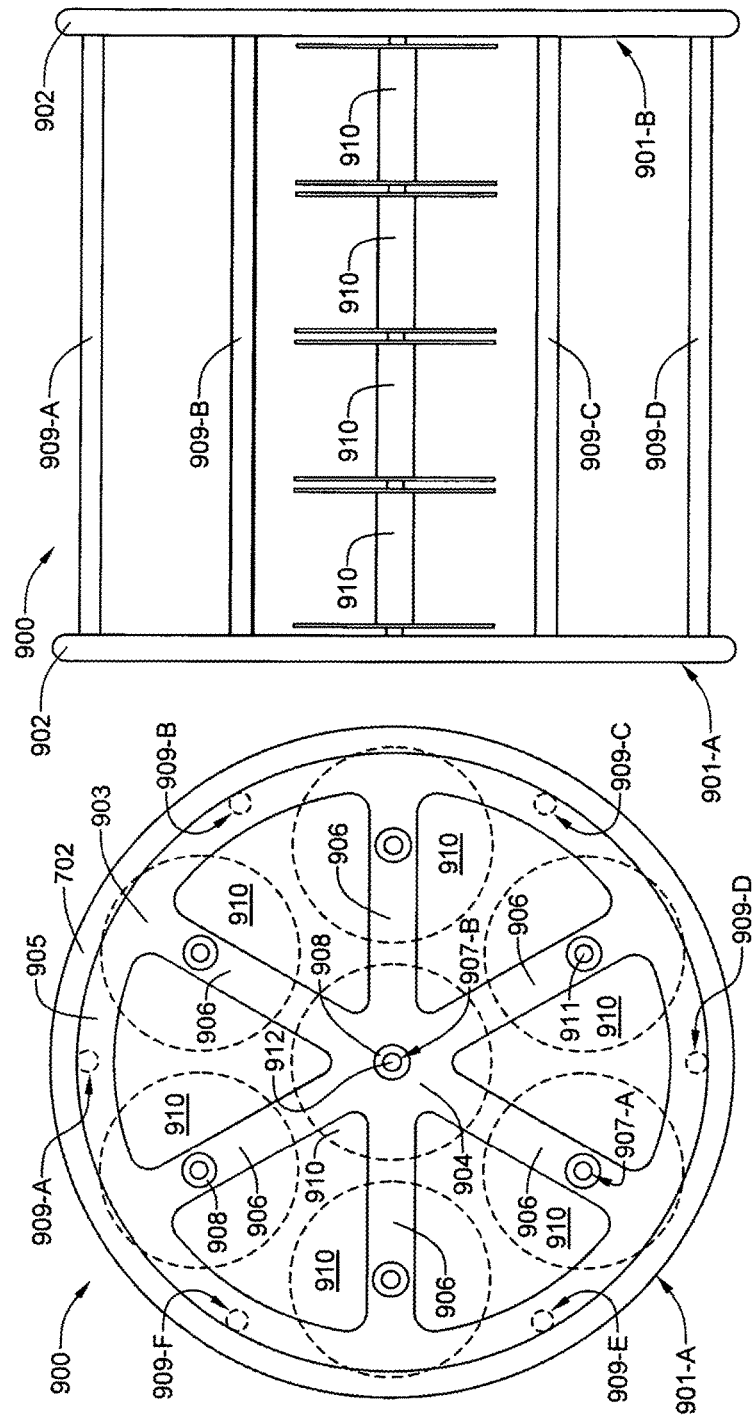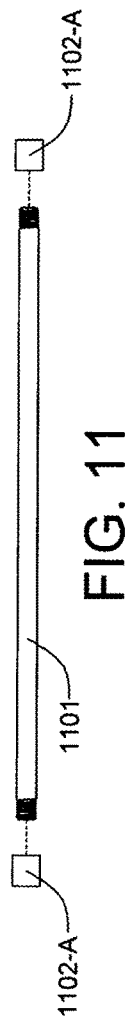

Spooly

Spooly parts are cut up angle iron, or U or C channel. Holes for assembly are drilled and welded sub sections are bolted together reducing manufacturing costs.

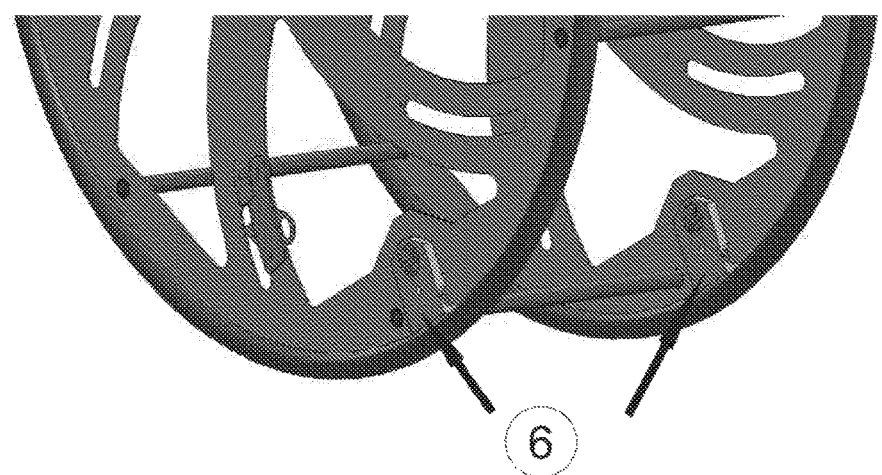
6
Swing out brake
in neutral position
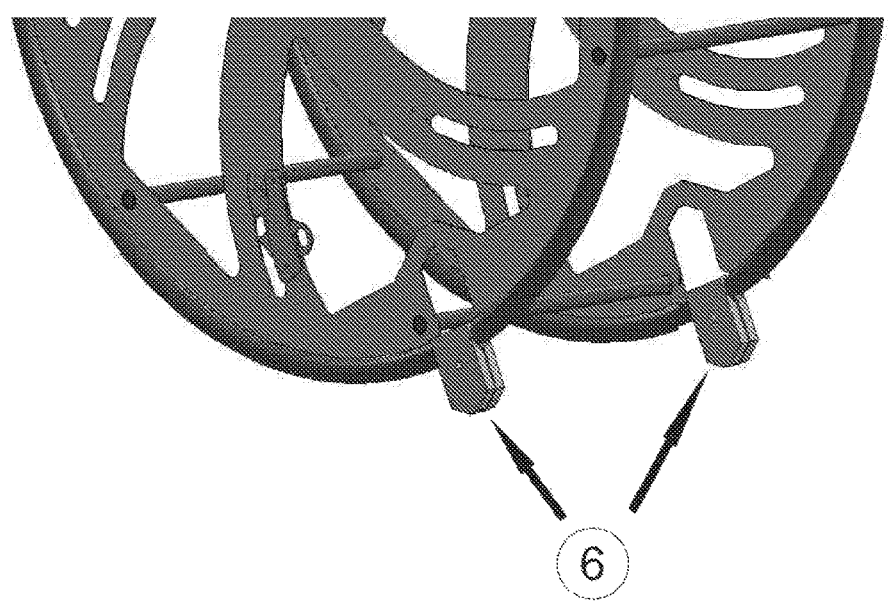
6
Swing out brake
in active position
FIG. 14

Two units can be attached side by side to increase capacity and efficiency

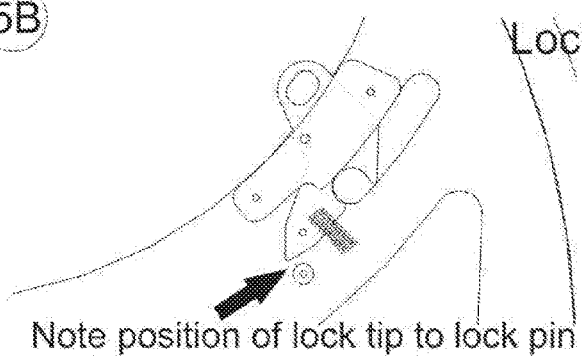
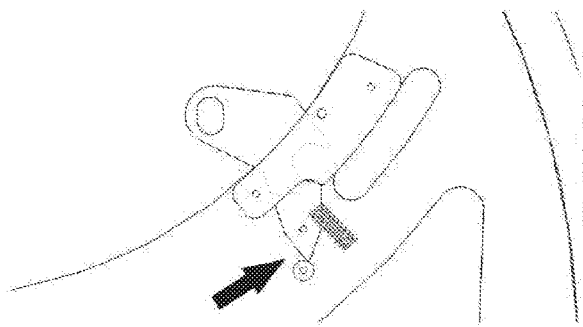
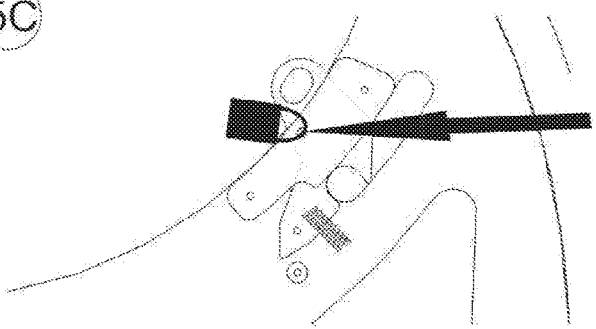
FIG. 18

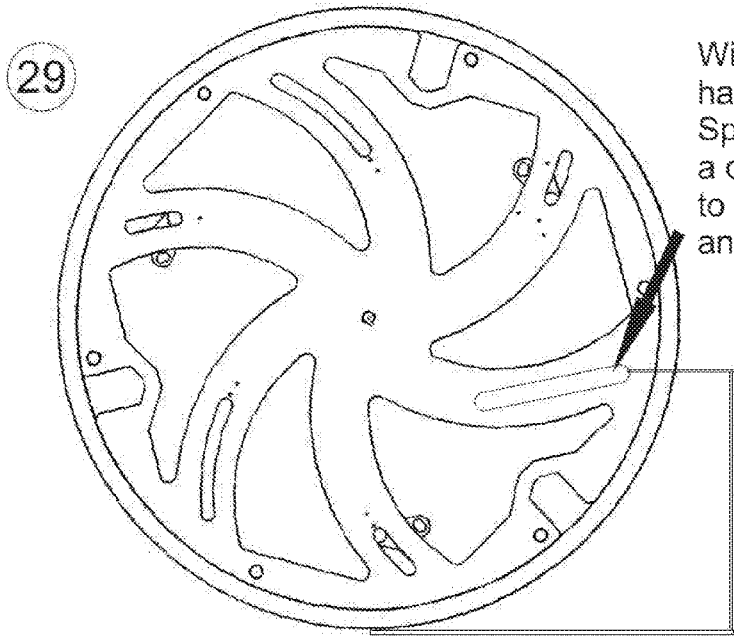
With a straight slot you have to rotate the Spoolhauler further at a disadvantaged angle to get the axle to roll and set into the lock
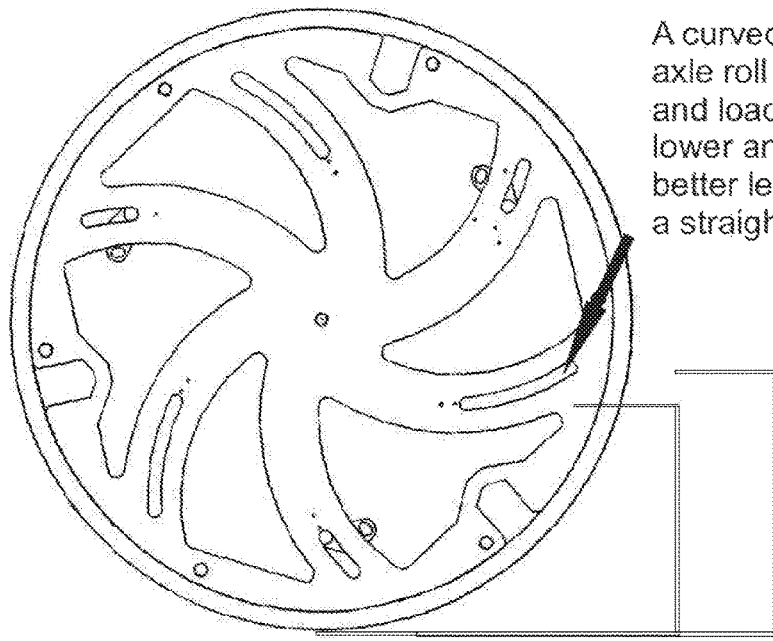
A curved slot lets the axle roll more gently and load sooner at a lower angle and better leverage than a straight slot.
Straight slot heighth
FIG. 19

ROLLABLE WIRE DISPENSING SPOOL RACK

This application claims priority to Provisional Patent Application No. 61/480,113 filed Apr. 28, 2011, and application Ser. No. 13/506,597 filed Apr. 30, 2012 and the contents of which are incorporated by reference.

FIELD OF THE INVENTION

This invention relates, generally, to construction tools and equipment used by electricians and, more particularly to racks designed to hold multiple spools of wound wire and cable.

BACKGROUND OF THE INVENTION

The installation of electrical wires and cables at a construction site is normally accomplished in a series of steps. For commercial and industrial construction, electrical boxes and conduits are installed on the walls or in the framed structure of the building. It is not unusual for the space between floors or spaces above drop ceilings to be used for runs of conduit and cable. Secondly, insulated copper conductors are pulled through the conduits and into the boxes. Thirdly, the conductors cut to appropriate lengths, insulation is stripped from the end of each conductor, some conductors are connected to others in the same box, and fixtures, switches, outlets, and other electrical devices are connected to the ends of the remaining conductors. For residential construction (and even for some light commercial and office construction), electrical boxes are installed in the framing of the building. Secondly, holes are drilled in the framing for runs of cable between the electrical boxes. Thirdly, cables having multiple copper conductors are pulled through the holes in the framing and into the electrical boxes. Fourthly, the cables are cut to an appropriate length, protective sheathing is removed from the end of each cable, with a small amount of sheathing remaining where it enters the electrical box. Fifthly, insulation is stripped from the ends of each of the conductors, come conductors are connected to others in the same box, and fixtures, switches, outlets and other electrical devices are connected to the ends of the remaining conductors. It will be appreciated by those skilled in the art that these three steps require a substantial amount of materials and labor, both of which affect the overall cost of the electrical work. Those skilled in the art of electrical work recognize that the process of installing electrical wiring in aircraft and ships most closely resembles the process used for installing electrical wiring in commercial buildings.

Electrical cables are frequently obtained from the manufacturer in a corrugated paperboard box. A center portion of one side of the box is removable so that one end of the cable can be pulled from the box. As the box does not rotate as the cable is extracted, twists are imparted to the cable. Single conductor insulated wire is almost always provided on a spool, which can be placed on an axle so that the wire can be unwound from the spool without imparting twists to the wire. In larger quantities, cable is also available on spools. For commercial wiring work, it is frequently necessary to pull many individual conductors at once through a single conduit. In order to prevent the wires from becoming tangled during the pulling operation, and to minimize the cross-sectional area of the pulled bundle, it is essential that the wire either be laid out on the ground in a bundle having no twists, or that the individual wires be unwound simultaneously from a rack on which the spools are mounted on axles so that the wire bundle can be pulled through the conduit without twists, kinks, or tangles. The task is made more difficult by the fact that wires may be of different size (i.e., current carrying capacity), and provided on different diameter spools. In the case of commercial buildings or similar structures, typically on the order of six to twelve or more wires may be pulled at the same time. In the case of large aircraft and large ships, the simultaneous pulling of between forty and sixty wires through electrical conduits is not uncommon.

Electricians are not the only tradesmen who routinely need to dispense multiple wires and/or multiple cables. Television cable installers and computer network installers have similar needs. For all of these applications, a wire and/or cable dispenser should have certain characteristics to provide maximum efficiency and convenience for the user. First, a dispenser of electrical wire or cable (hereinafter 30 referred to as a wire/cable dispenser) should hold a plurality of wire/cable spools. Second, the wire spools should be directly observable to check the amount of wire remaining on each spool. Third, each wire spool should be easily replaceable when it becomes exhausted, with the removal of other spools being held to an absolute minimum. Fourth, the wire spools held by the wire/cable dispenser should not free spin in a coasting manner as the wire is dispensed therefrom. Free spinning is a problem 5 because it can cause tangles as the wire is unwound. Fifth, the wire/cable dispenser should be portable. That is to say that it should be capable of being readily transported between work sites and manually movable to different areas if a particular job site. Finally, the wire/cable dispenser should be easily locked in a desired location so that it does not creep or roll as wire or cable is dispensed therefrom.

Electrician racks and carts, on which spools of wire can be mounted for the simultaneous, untangled and unkinked unwinding of multiple wires have likely been available for more than a hundred years. Over that period, available racks and carts have become generally more transportable, lighter in weight and better adapted to electrical installation work. As will be seen from the following descriptions, a plethora of electrician wire rack and cart patents have been patented.

U.S. Pat. No. 1,230,591 to Lou Gray discloses an inclined display rack for holding spools of wound electric wire of various grades and gages. The rack is designed such that wire from multiple spools may be unwound simultaneously. The rack, though lacking wheels, could be moved to different locations, either with the spools of wire in place, or by removing the spools and moving the rack and spools separately.

U.S. Pat. No. 2,957,644 to Gerald M. Beardslee discloses a conveniently transportable rack for retaining a plurality of spools of wire on tubular latched cross supports. Wire can be dispensed from multiple spools simultaneously.

U.S. Pat. No. 3,856,230 to Edward J. Zimmer discloses a wire dispensing cart that is combination of a two-wheeled hand dolly and a rigid supplemental frame superstructure that is adapted to hold a plurality of axles in a ladder like configuration. At least one spool of wire can be suspended from each of the axles. Wire can be dispensed from one or more spools simultaneously.

U.S. Pat. No. 4,533,091 to Reed H. Knight discloses a portable multiple-spool wire dispenser. The wire dispenser includes two brackets adapted to mount on the spaced-apart support legs of a step ladder, and a spool-supporting shaft spanning the distance between the brackets and secured to each of them. The shaft is mounted so that one end thereof can be swung out for adding or removing spools.

U.S. Pat. No. 5,188,308 to Norman P. Tussing discloses a cart for use by 5 electricians, which has a main longitudinal member supported at its ends by pairs of wheels with one pair being of the swivel type to facilitate passage through narrow doorway openings of a building. End-mounted post assemblies on the longitudinal member are equipped with arms for the optional carrying of wire reels or electrical conduit. Each post assembly includes at least one sleeve through which may be inserted a spindle on which a large reel of wire may be carried.

U.S. Pat. No. 5,275,349, also to Norman P. Tussing, discloses a cart for transporting wire spools as a job site and having a tee-shaped frame with a three wheel undercarriage. A spool support includes a post with arms on which wire spools are rotatably carried.

U.S. Pat. No. 5,285,981 to Steven M. Pavelka discloses a spooled wire dispenser cart, which includes a central frame and a plurality of spaced spool bars. At the free end of each spool bar is a spool retainer. Each spool retainer includes an elongate element which has an unblocking position relative to the spool bar, which permits wire spools to be freely slid over the free end of the spool bar and a blocking position which prevents wire spools from sliding over the free end of the spool bar. The wire cat may also include a folding handle having an extended maneuvering position.

U.S. Pat. No. 5,308,012 to Carsen S. Fuller discloses a folding wire cart convertible into a float and handtruck. The wire cart has a body rotatably attached to a base, main wheels secured to the base, and a handtruck handle. Additionally, the 25 convertible folding wire cart has a float handle and swivel wheels spaced apart from the main wheels and adjacent the handtruck handle so that the wire cart may also be used in a float configuration.

U.S. Pat. No. 5,316,232 to John A. Lambert, Jr. discloses an omnidirectional wire dispenser for transporting and dispensing single and multiple wires in any direction. The wire dispenser comprises a boxlike outer frame, with wheeled legs, a parallel inner shaft, with perpendicular spool holders thereon, and spool tension bars. The top out frame contains individual wire guide windows, which permit omnidirectional dispensing of one or more wires from spool holders without repositioning the dispenser.

U.S. Pat. No. 5,687,928 to Daniel T. Lassiter discloses a rack for rotatably mounting one or more wire dispensing spools. A set of four rollers extend horizontally 5 between a pair of spaced parallel side walls and are positioned in a generally square-shaped configuration and rotatably mount and retain the spools therebetween. Each roller includes a cylindrical low-friction plastic sleeve mounted on a center support rod or axle. A plurality of spacers separate the sleeve into a plurality of sleeve sections, thereby allowing the spools to rotate independently of each other without affecting the rotation of adjacent spools. A top roller of each set is spring biased and moves horizontally within a pair of aligned slots formed in the spaced side walls, thereby allowing the spring biased roller to move horizontally toward and away from the other top roller of each set so that the spools may be easily inserted or removed from the rack. Front and rear wheels and a handle allow the rack to used as a cart to transport the spools and other equipment and materials to and from the work site.

U.S. Pat. No. 5,944,280 to Angelo S. Dimitri discloses a hand-carried wire spool rack for dispensing wire. The rack includes a frame having a pair of horizontally extending parallel members for rotatably supporting at least one removable wire spool. The members are spaced apart by a distance that is less than the diameter of the spool. An upper member is secured to the frame and extends parallel with one of the parallel members. The upper member is positioned upwardly and outwardly from one of the parallel members. The wire spool is positionable in a first position in rotatable supported engagement with one of the parallel members and the upper member when a dispensing force is exerted on the wire spool which is generally greater than the relative weight of the wire spool.

U.S. Pat. No. 5,887,819 to Francis Korn, et al. discloses a rack for dispensing wire or tubing from spools rotatably mounted on a rod supported at its ends by retaining slots in opposing sides of a rectangular frame.

U.S. Pat. No. 5,967,451 to HristosRadaios discloses a carrier for one or more rotatably-mounted spools of wire. The carrier is portable, and is suitable for the separate or simultaneous dispensing of wire from one or more wire spools housed within the carrier. The carrier includes a central rod, which is inserted through the center of each spool. The carrier further includes a generally semi-circular cradle positioned below the wire spools. A pair of end walls supports the semi-circular cradle. Channels in the end walls permit rotation of the cradle relative to these end walls. The 5 channels are formed by a generally circular cut-out in each of the end walls. The carrier also includes one or more slots in the cradle for the passage and dispensing of the wire through these slots.

U.S. Pat. No. 6,116,533 to Doyle Elder discloses a wheeled dispenser for dispensing wire from spools. The dispenser has a rectangular frame, three stationary vertical posts, and two rotatable vertical posts each located between two stationary posts. Each rotatable post has a plurality of laterally projecting rods for supporting spools. The rotatable post can be rotated to a first position such that the rods are accessible for loading spools, and rotated to a second position wherein each rod can latch to an adjacent stationary post, with the spools held parallel so that they all pay out wire in one direction. The dispenser also has wheels and a handle which can incline relative to the frame. A pin arranged to close a clevis secured the handle in a substantially upright position relative to the frame.

U.S. Pat. No. 6,182,920 to David G. Watkins discloses a collapsible dolly for dispensing cable or wire from spools mounted thereon. The dolly includes a frame 20 body having first and second ends, a substantially vertical support having upper and lower ends and an inclined support having first and second ends, with at least one of the supports including a spool axle. The lower end of the vertical support is releasably pivotally affixed to the first end of the body, the first end of the inclined support is releasably affixed to the upper end of the vertical support and the second end of the inclined support is releasably pivotally affixed to the second end of the body. The dolly also includes an optional handle releasably pivotally affixed to the second end of the body and interchangeable with an extendible elevating cable boom.

U.S. Pat. No. 6,270,094 to William F. Campbell discloses a wire dispensing utility cart adapted to carry wire spools for dispensing wire during installation. A relatively large utility cart is provided for carrying multiple large spools of wire in a mobile fashion for dispensing wire during the installation of electrical wiring in buildings, structures, aircraft, and the like. The cart provides at least two elongated storage bays to facilitate transportation of relatively large objects such as ladders, conduits and other materials and supplies needed for the installation process.

U.S. Pat. No. 6,422,504 to Doyle W. Elder discloses an easily-maneuvered, 5 four-wheeled cart upon which a number of spools of wire, or other spooled material, of either like size or different sizes can be rotatably mounted along an inclined plane such that wires can be pulled from multiple spools without becoming entangled one with another. A wire guide aids in bringing the various wires together as a bundle for pulling as a single unit.

U.S. Pat. No. 6,523,777 to Michael F. Gaudio discloses a portable wire spool caddy for releasably holding at least one cylindrical spool having an outer diameter while a wire or the like is being unwound from the spool. The caddy comprises an elongated frame which includes first and second spaced apart ends, a plurality of generally parallel fixed rods which each extend between and are connected to the first and second ends, and at least one movable rod which is generally parallel to the fixed rods and which extends between and is pivotably connected to the first and second ends. The movable rod is pivotable between a first position in which the movable rod is separated from an adjacent fixed rod by a second distance that is less than the diameter of the spool, and a second position in which the movable rod is separated from the adjacent fixed rod by a third distance, which is greater than the diameter of the spool. When the movable rod is in its first position, the spool is retained between the movable rod and the fixed rods, and when the movable rod is in its second position, the spool may be removed or inserted between the movable rod and the adjacent fixed rod. U.S. Pat. No. 7,150,459 to Jay Anderson, et al. discloses a manually-operated wheeled reel support and dispensing cart for supporting multiple reels of material and for dispensing the material from the reels. The cart includes a cart frame having spaced side members, handles for manual cart handling and a top cross brace, which the frame being connected to a support plate and wheel assembly. A plurality of spindle hinge elements, each having a pivot opening, are fixed in spaced relation on one of the frame side members and receive L-shaped removable spindle elements for pivotal opening and closing movement. When open, the spindle elements are supported so that reels can be added or removed. When the spindle elements are closed, the secure reels of material to the cart.

U.S. Pat. No. 7,243,876 to Clyde R. Robison discloses an apparatus for handling wire spools. The apparatus includes a brace and a spool handle removably connected to the base. A spool is mounted on the handle and thereafter a user picks up the handle and mounts it on the base. Thereafter, wire can be dispensed from the spool.

U.S. Patent Publication 2007/0120003 for Geoffrey L. Grant discloses a caddy for spooled materials, which facilitates the removal and installation of spools of coiled materials (wire, cable, rope, cord, chain, etc.) within the device, while positively retaining the spools as material is withdrawn. The caddy includes a pair of opposed lateral frame members having a series of fixed crossmembers therebetween, which define a spool retaining cradle therein. A pivotally mounted arm extends from each frame member adjacent the first or rear fixed crossmember, with a spool retaining crossmember connecting the distal ends of the arms. When the movable cross-member is raised, sufficient room is provided between the first fixed crossmember and movable crossmember to allow a spool to be placed within or removed from the caddy. However, when the movable crossmember is lowered, the space between the first fixed crossmember and the movable crossmember is reduced to less than the diameter of the spool, thereby securing the spool in place.

U.S. Pat. No. D584,471 to Johannes Petrus Louis Diedericks discloses a wire and cable spool cart having a frame with a longitudinal backbone and two transverse supports at opposite ends thereof. Each of the transverse supports is equipped with a spaced apart swiveling wheel assemblies. An inverted L-shaped support, which is affixed to one end of the frame, is equipped with a plurality of transverse horizontal spool-mounting tubes, which extend from both sides of the L-shaped support. Multiple spools of wire may be placed on each end of a spool-mounting tube. Each end of a spool-mounting tube is equipped with a spool retainer.

U.S. Pat. No. 7,481,394 to John T. Gleason discloses a caddy for carrying spools of electrical wire. The caddy has complementary T-shaped slots in opposite side walls and members affixed between the side walls that support the spools, forming a cage, and one member rides within the T-shaped slot. The moving member may be pulled away from the cage to allow for room to release a spool from its cage, but the member will move by itself in response to movement of the caddy to keep the spool or spools locked within the cage.

U.S. Patent Publication 2010/0078514 for Jerry L. Thompson discloses a portable wire spool holding device that includes at least two separate mechanical devices for supporting a cross bar between two vertical supports. Each mechanical device can be comprised of three primary components: two gripping elements connected by a leveraged bar support element. The leveraged bar support element can be adapted to hold a cross bar member.

The heretofore described electrician racks and carts have one or more deficiencies. Some are overly complicated; others are unwieldy; others are not particularly portable; others are difficult to and still others are unnecessarily heavy. What is needed is a new type of carrier for spools wound with electrical wire and/or cable. The carrier should be relatively inexpensive, easy to manipulate, ultra compact, lightweight, easy to move without having to lift and carry it, simple to manufacture, easily rendered unmovable for the pulling of multiple wires, and capable of holding a number of spools of wire sufficient for serious electrical installation work.

SUMMARY OF THE INVENTION

In one aspect, a rollable dispenser for spooled wire includes equiangular-spaced tubular braces which rigidly interconnect frames adjacent circular peripheral edges. One or more wire spools are retained between the platters on removable axles which span the distance between both platters at radial intervals. One or more spools may also be retained by a centrally positioned axle.

In the preferred embodiment, each platter is constructed from a length of circularly bent tubing, the ends of which are butt welded together to form a hoop. Each platter further includes a circular laminar plate that includes a circular rim, a central hub having a single axle aperture, and radial laminar spokes, each having an axle aperture, which join the rim to the hub. In one implementation, the dispenser looks like a large hose reel.

In another aspect, a rollable dispenser for spooled wire and/or cable looks much like a large reel for garden hose storage. Like many such reels, the circular, spaced-apart, parallel platters thereof are constructed from a circular rim, a plurality of radial spokes, and a central disc, with the spokes interconnecting the rim and the central disc. However, instead of the spaced-apart, parallel platters of the reel being held together by a central cylindrical core, they are held together by equiangularly-spaced tubular braces which rigidly interconnect the platters near their peripheral edges. The spokes of each platter are radially aligned with those of the opposite platter. One or more wire spools are retained between the platters on removable axles which span the distance between the radially-aligned spokes of both platters. One or more spools may also be retained by an axle passing through the reel's central axis.

In a preferred embodiment, the circular rim of the platter is constructed from a length of circularly-bent tubing, the ends of which are butt welded together to form a hoop. Each of the radial spokes is constructed from a length of steel channel stock. The central disc is surrounded by a cylindrical wall, which is either formed with the disc in a single stamping or welded to the periphery of the disc. The inner ends of the spokes are welded to the cylindrical wall, with the spoke channels and the wall of the central disc facing one direction, which will be the outer platter of the platter. The outer ends of the spokes are welded directly to the hoop so that the flat major surface of each spoke is coplanar with the inner surface of the hoop. This configuration will enable spools of wire to be installed within the rolling spool rack without the hoop interfering with the entry thereof into the rack. An arcuate gusset reinforces each section of hoop between each pair of adjacent spokes, and is welded to the hoop, as well as to each of the adjacent spokes. Each spoke is equipped with one or two axle apertures, which each axle aperture accommodating different spool sizes. Each axle aperture is reinforced with a surrounding flat washer that is welded to the spoke. For smaller-diameter embodiments of the invention, the entire central portion of the platter (i.e., spokes and central disc) can be stamped or cut from a single piece of steel plate stock. This can even be done for the larger-diameter embodiments, but with substantial waste of steel between the spokes. Once a pair of platters has been fabricated, they are positioned parallel to one another, with the spokes and arcuate gussets of one platter radially aligned with the spokes and gussets, respectively, of the other platter. Each end of a tubular brace is then welded to a middle region of a gusset of each radially aligned pair of gussets, thereby interconnecting the platters, yet still leaving sufficient space to insert spools into the rollable rack from the periphery thereof. The tubular braces are radially spaced so that spools containing wound wire can be placed between the platters and mounted on a removable axle which spans the distance from one platter to the other. Each axle is preferably fabricated from a length of pipe that has been threaded on both ends. Retaining nuts are most easily made by sawing a pipe coupler in a direction that is perpendicular to the coupler's central axis.

In one implementation, the rollable, spooled wire dispenser can be prevented from rolling by locking it in place with a chock modeled after those which have been used to chock airplane wheels for nearly a century. The rollable wire/cable dispenser can be manufactured in various diameters and in various widths to accommodate wire spools of different sizes and widths. Presently preferred embodiments of the invention are built with 60-inch, 48-inch, and 24-inch outplatter diameters. A 60-inch-diameter embodiment having a width of 37 inches can accommodate up to six 23.5-inch-diameter, 16-inch-wide spools (two spools on every other radially-spaced axle) wound with up to 2500 feet of #6 insulated wire and three 15.5-inch-diameter, 9.5-inch-wide spools (three spools on the central axle) wound with up to 1000 feet of #6 or #8 insulated wire. Alternatively, the 60-inch diameter embodiment can accommodate twenty-one 15.5-inch-diameter spools (three spools on each radially-spaced axle and three spools on the central axle) wound with up to 1000 feet of #6 or #8 insulated wire. A 48-inch-diameter embodiment having a width of 34 inches accommodates up to twenty-one 15.5-inch-diameter, 9.5-inch wide spools (three per axle) wound with up to 2500 feet of #10 or #12 insulated wire. A 24-inch-diameter embodiment having a width of 23.5 inches accommodates up to twenty-eight 7-inch-diameter, 5-inch-wide spools (two per axle) wound with up to 500 feet of #14 or #16 insulated wire.

Advantages of the above systems may include one or more of the following. The wire and cable can be selectively dispensed by unwinding it from the spools, as needed, during installation thereof in a building or other large structure. The fabrication process results in a structure that can be easily rolled from one location to another, and which can be rolled up or down a loading ramp. The circular hoop on each platter serves several functions: it strengthens the outer edges of the platter, reduces rolling and turning friction, and minimizes the likelihood that the outer edges of the bobbin will cut items over which it might roll (e.g., worker's toes).

BRIEF DESCRIPTION OF THE DRAWINGS

FIG. 1 is a side elevational view of a first embodiment 60-inch-diameter rolling spool rack;

FIG. 2 is front or rear elevational view of a first embodiment 60-inch-diameter embodiment rolling spool rack having a width of 37 inches;

FIG. 5 is a side elevational view of a second embodiment 60-inch-diameter rolling spool rack showing a configuration for installation of 23.5-inch-diameter, 16-inch-wide spools (four are shown mounted on four different, radially-spaced axles);

FIG. 6 is front or rear elevational view of a second embodiment 60-inch-diameter embodiment rolling spool rack having a width of 37 inches showing a frontal (or rear) configuration for installation of 23.5-inch-diameter, 16-inch-wide spools (two are shown mounted on a single axle);

FIG. 9 is a side elevational view of a 24-inch-diameter embodiment of a rolling spool rack, showing a configuration for installation of 7-inch-diameter, 5-inch-wide spools (six are shown mounted on different, radially-spaced axles, and one is shown 25 mounted on a central axle);

FIG. 10 is front or rear elevational view of a 24-inch-diameter embodiment of a rolling spool rack having a width of 23.5 inches, showing a frontal (or rear) configuration for installation of 7-inch-diameter, 5-inch-wide spools (four are shown mounted on a single axle);

FIG. 11 is a plan view of a single axle and a pair of retainer nuts;

FIGS. 13-20 show details for one rollable dispenser embodiment.

PREFERRED EMBODIMENT OF THE INVENTION

Figure 4:
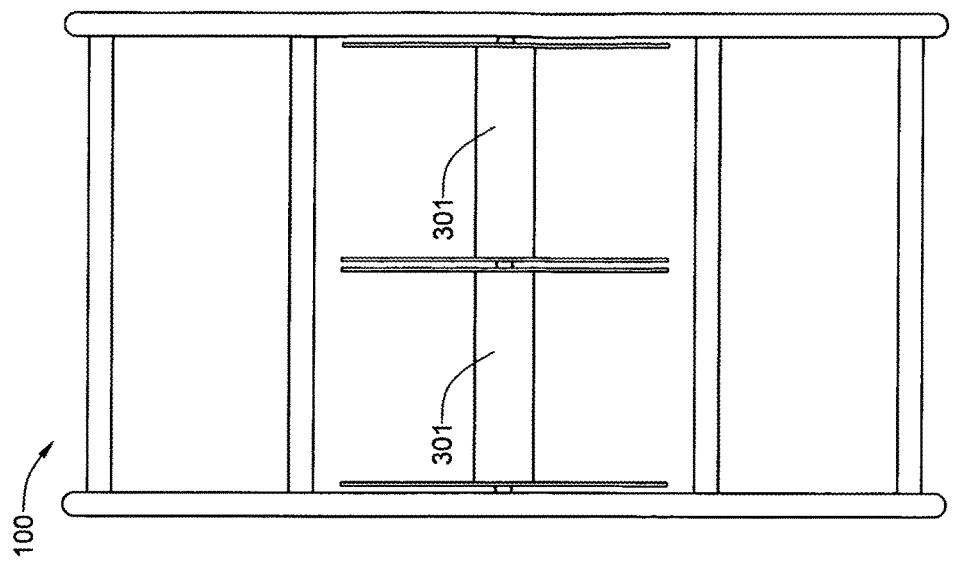
FIG. 4 is front or rear elevational view of the first embodiment 60-inch-diameter embodiment rolling spool rack having a width of 37 inches showing a frontal (or rear) 5 configuration for installation of 23.5-inch-diameter, 16-inch-wide spools (two are shown mounted on a single axle)

Various embodiments of the rolling wire spool rack will now be described in detail, with reference to the attached drawing FIGS. 1 through 13. It should be understood that the drawings are not, necessarily, drawn to scale, and that they are 5 intended to be merely illustrative of the invention.

Referring now to FIG. 1, a first embodiment 60-inch-diameter rolling spool rack 100 is seen in a side view, which shows only one platter 101-A of two identical, spaced-apart circular platters 101-A and 101-B (item number 101 applies to either). Each of the platters 101 is fabricated from a peripheral hoop 102, a central disc 103, and plurality of radially-spaced spokes 104, which interconnect the central disc 103 to the peripheral hoop 102. The hoop 102 is constructed from a length of circularly-bent tubing, the ends of which are butt welded together, thereby forming the hoop 102. Each of the spokes 104 is constructed from a length of steel channel stock. The central disc 103 is, preferably, surrounded by a cylindrical wall 105, which is either formed with the disc 103 in a single stamping or welded to the periphery of the disc 103. The inner end 106 of each spoke 104 is welded to the cylindrical wall 105, with the spoke channels 107 and the cylindrical wall 105 on one side of the platter 101, which will be the outer side thereof. The outer end 108 of each spoke 104 is welded directly to the hoop 102, so that the flat major surface of each spoke (i.e., the surface behind the channel 107) is coplanar with the inner surface of the hoop 102. This configuration will enable spools of wire to be installed within the rolling spool rack without the hoop interfering with the entry thereof into the rack. An arcuate gusset 109 reinforces each section of hoop 102 between each pair of adjacent spokes 104, and is welded to the hoop 102, as well as to each of the adjacent spokes 104. Each spoke is 104 equipped with two axle apertures 110-A and 110-B, with each axle aperture on a single spoke 104 accommodating the mounting of spools of different diameters. In addition, the central disc is also equipped with a single axle aperture 110-C. Each axle aperture 110-A, 110-B, and 110-C is reinforced with a surrounding flat washer 111 that is welded to the spoke 104. It should be noted that the positions of the hidden tubular cross braces are indicated by six broken-line circles 112-A, 112-B, 112-C, 112-D, 112-E and 112-F (item number 112 applies, generally, to any of the six tubular cross braces of the first embodiment 60-inch-diameter rolling wire spool rack 100). The ends of each tubular cross brace 112 are welded to two opposing arcuate gussets 109 on opposite platters 101.

Referring now to this FIG. 2, the first embodiment 60-inch-diameter rolling 5 spool rack 100 is seen in a front or rear view, in which both platters 101-A and 101-B are visible. This particular embodiment has a width of 37 inches so that it can accommodate two 23.5-inch-diameter, 16-inch-wide spools on a single axle. The two platters 101-A and 101-B are held together by the tubular cross braces 110-A, 110-B, 110-C, 110-D, 110-E and 110-F.

Figure 3:
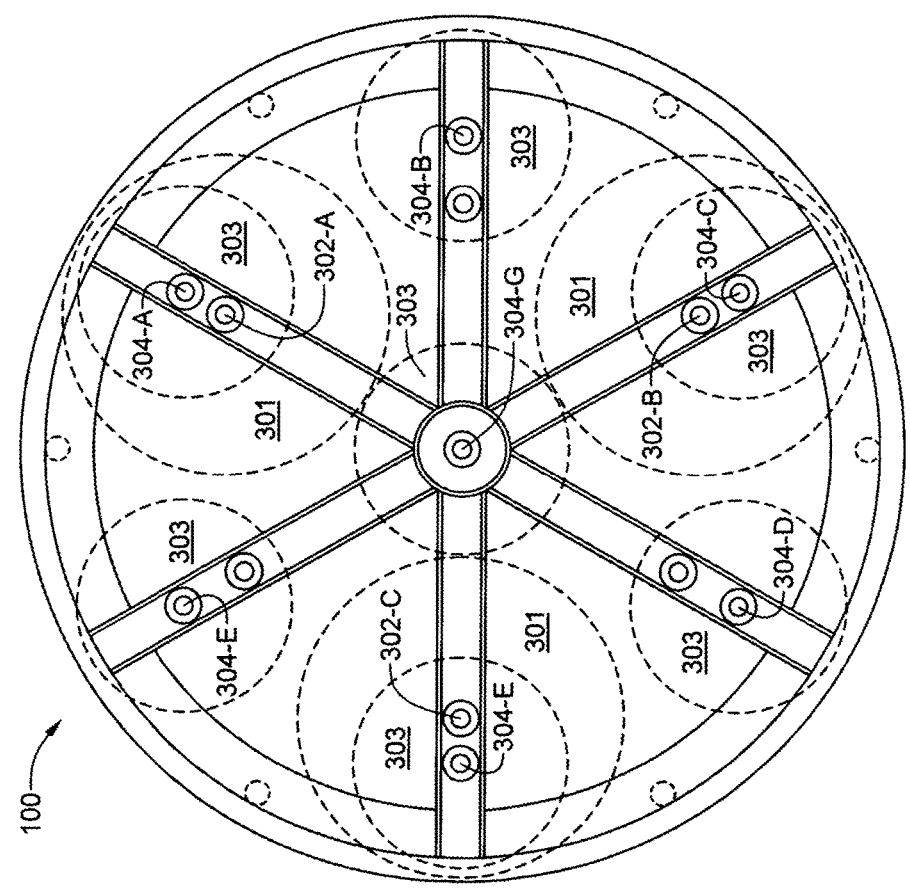
FIG. 3 is a side elevational view of the first embodiment 60-inch-diameter 30 rolling spool rack showing a configuration for installation of 23.5-inch-diameter, 16-inch-wide spools (three are shown mounted on three different, radially-spaced axles) and 15.5-inch-diameter, 9.5-inch-wide spools (six are shown on different, radially-spaced axles and one is shown on a central axle)

Referring now to FIG. 3, this side view of the first embodiment 60-inch-diameter rolling spool rack 100 shows alternative configurations for the installation of 23.5-inch-diameter, 16-inch-wide spools 301 on three different, equiangularly-spaced axles 302-A, 302-B and 302-C in a first circular pattern 303, and for the installation of 15.5-inch-diameter, 9.5-inch-wide spools 303 on seven different axles-six radially-spaced axles 304-A, 304-B, 304-C, 304-D, 304-E, 304-F and one central axle 304-G. Referring now to FIG. 4, this front or rear elevational view of the first embodiment 60-inch-diameter embodiment rolling spool rack having a width of 37 inches shows a frontal (or rear) configuration for the installation of two 23.5-inch-diameter, 16-inch-wide spools 301 on a single axle 302-A. With two spools mounted on axles 302-A, 302-B and 302-C, this rolling spool rack 100 is capable of holding a total of six 23.5-inch-diameter, 16-inch-wide spools 301, in addition to up to three 15.5-inch-diameter, 9.5-inch-wide spools 303 on the central axle 304-A. As three 15.5-inch-diameter, 9.5-inch-wide spools 303 may be mounted on each of axles 304-A, 304-B, 304-C, 304-D, 304-E, 304-F and 304-G, this rolling spool rack 100 is also capable of holding a total of twenty-one of those spools.

Referring now to FIG. 5, a second embodiment 60-inch-diameter rolling spool rack 500 is seen in a side view, which shows only one platter 501-A of two identical, spaced-apart circular platters 501-A and 501-B (item number 501 applies to either). Each of the platters 501 is fabricated from a peripheral hoop 102, a central disc 103, and plurality of radially-spaced spokes 502, which interconnect the central disc 103 to the peripheral hoop 102. The hoop 102, the central disc 103, and the cylindrical wall 105 are identical to those of the first embodiment 60-inch-diameter rolling spool rack 100. However, as there are only four spokes rather than six, each of the spokes 502 is constructed from a length of steel channel stock that is about fifty percent wider than the spokes 104 used for the first embodiment 60-inch-diameter rolling spool rack 100. 5 The inner end 503 of each spoke 502 is welded to the cylindrical wall 105, with the spoke channels 504 and the cylindrical wall 105 on one side of the platter 501, which will be the outer side thereof. The outer end 505 of each spoke is welded directly to the hoop 102, so that the flat major surface of each spoke (i.e., the surface behind the channel 504) is coplanar with the inner surface of the hoop 102. This configuration will enable spools of wire to be installed within the rolling spool rack without the hoop interfering with the entry thereof into the rack. An arcuate gusset 506 reinforces each section of hoop 102 between each pair of adjacent spokes 502, and is welded to the hoop 102, as well as to each of the adjacent spokes 502. Each spoke 502 is equipped with a single axle aperture 507. Each axle aperture 507 is reinforced with a surrounding flat washer 110 that is welded to the spoke 502. It should be noted that the positions of the hidden tubular cross braces are indicated by four broken-line circles 508-A, 508-B, 508-C, and 508-D (item number 508 applies, generally, to any of the four cross braces of the second embodiment 60-inch diameter rolling spool rack 500). The ends of each tubular cross brace 508 are welded to two opposing arcuate gussets 506 on opposite platters 501. Also shown in this side view is a configuration for the installation of 23.5-inch-diameter, 16-inch-wide spools 301 on four different, equiangularly-spaced axles 509 in a circular pattern. A central axle 510 provides an optional mounting location for smaller wire spools.

Referring now to this FIG. 6, the second embodiment 60-inch-diameter rolling spool rack 500 is seen in a front or rear view, in which both platters 501-A and 501-B are visible. The two platters 501-A and 501-B are held together by the tubular cross braces 508-A, 508-B, 508-C, and 508-D. This particular embodiment has a width of 37 inches so that it can accommodate two 23.5-inch-diameter, 16-inch-wide spools 301 in a side-by-side arrangement on a single axle, as is shown in this view. With two such spools on four axles, a total of eight spools can be mounted on this second embodiment 60-inch diameter rolling spool rack 500.

Figures 7, 8:
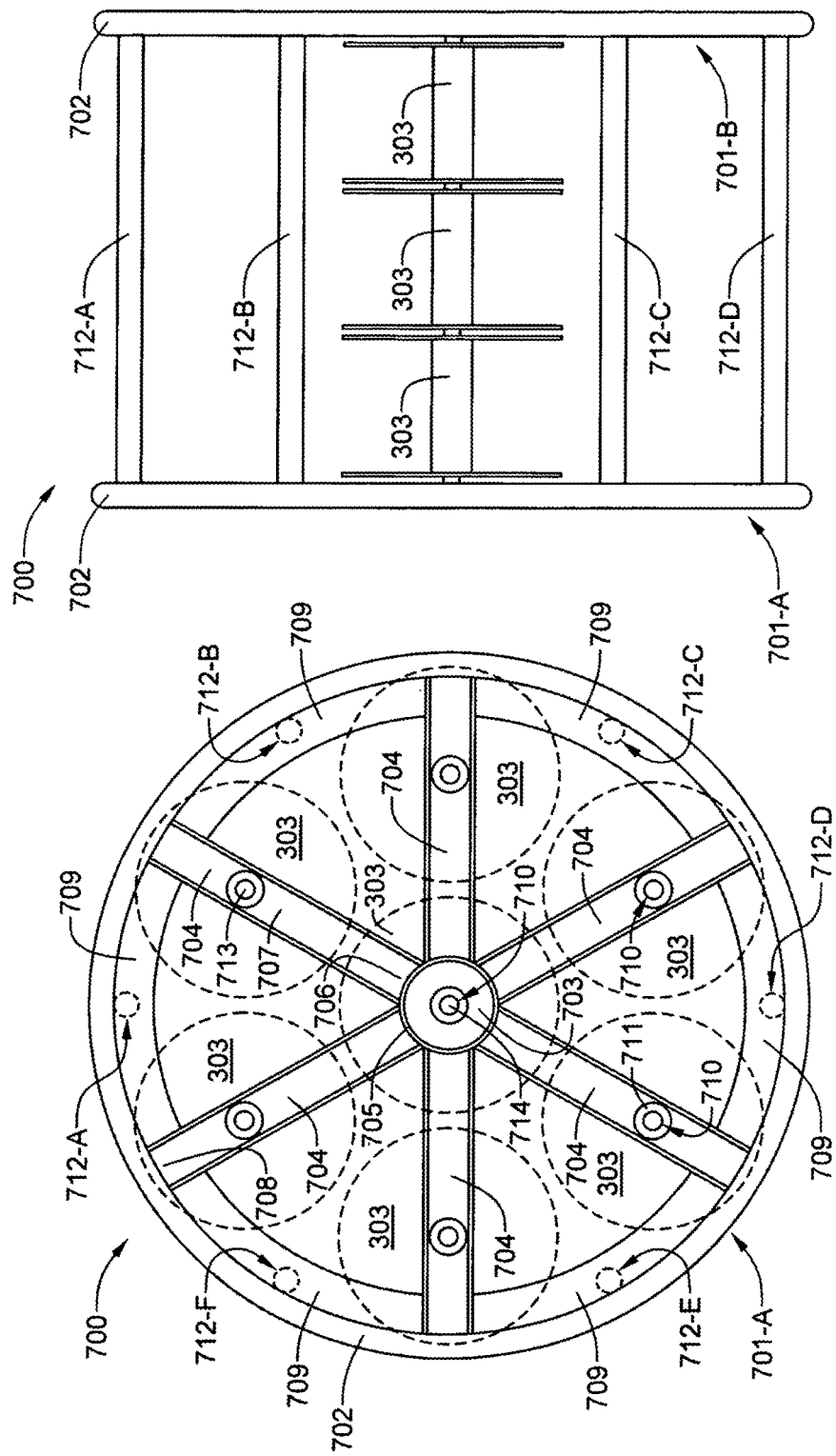
FIG. 7 is a side elevational view of a 48-inch-diameter embodiment of a rolling 15 spool rack, showing a configuration for installation of 15.5-inch-diameter, 9.5-inch-wide spools (six are shown mounted on different, radially-spaced axles, and one is shown mounted on a central axle)
FIG. 8 is front or rear elevational view of a 48-inch-diameter embodiment of a rolling spool rack having a width of 34 inches, showing a frontal (or rear) configuration 20 for installation of 15.5-inch-diameter, 9.5-inch-wide spools (three are shown mounted on a single axle)
Figure 12A:
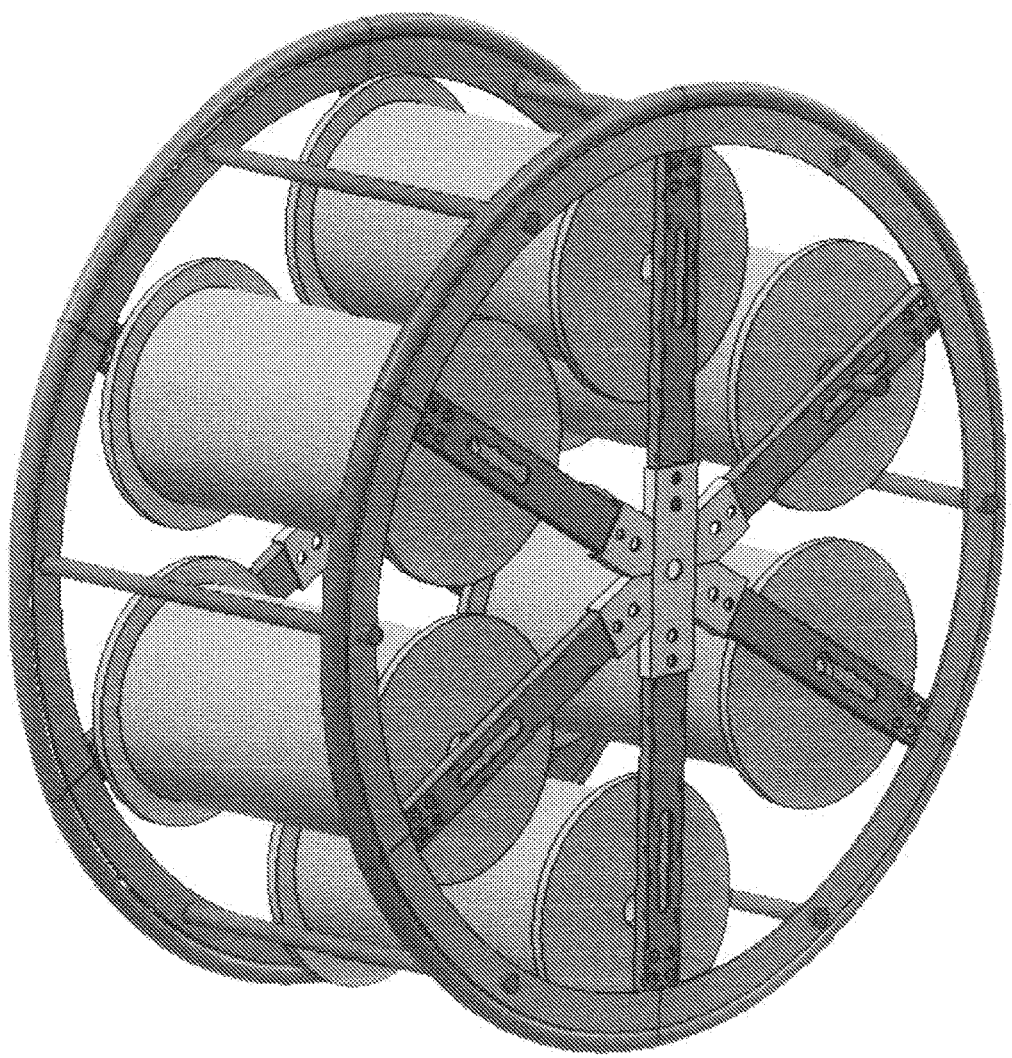
FIGS. 12A-12F show details for one rollable dispenser implementation.
Figure 12B:
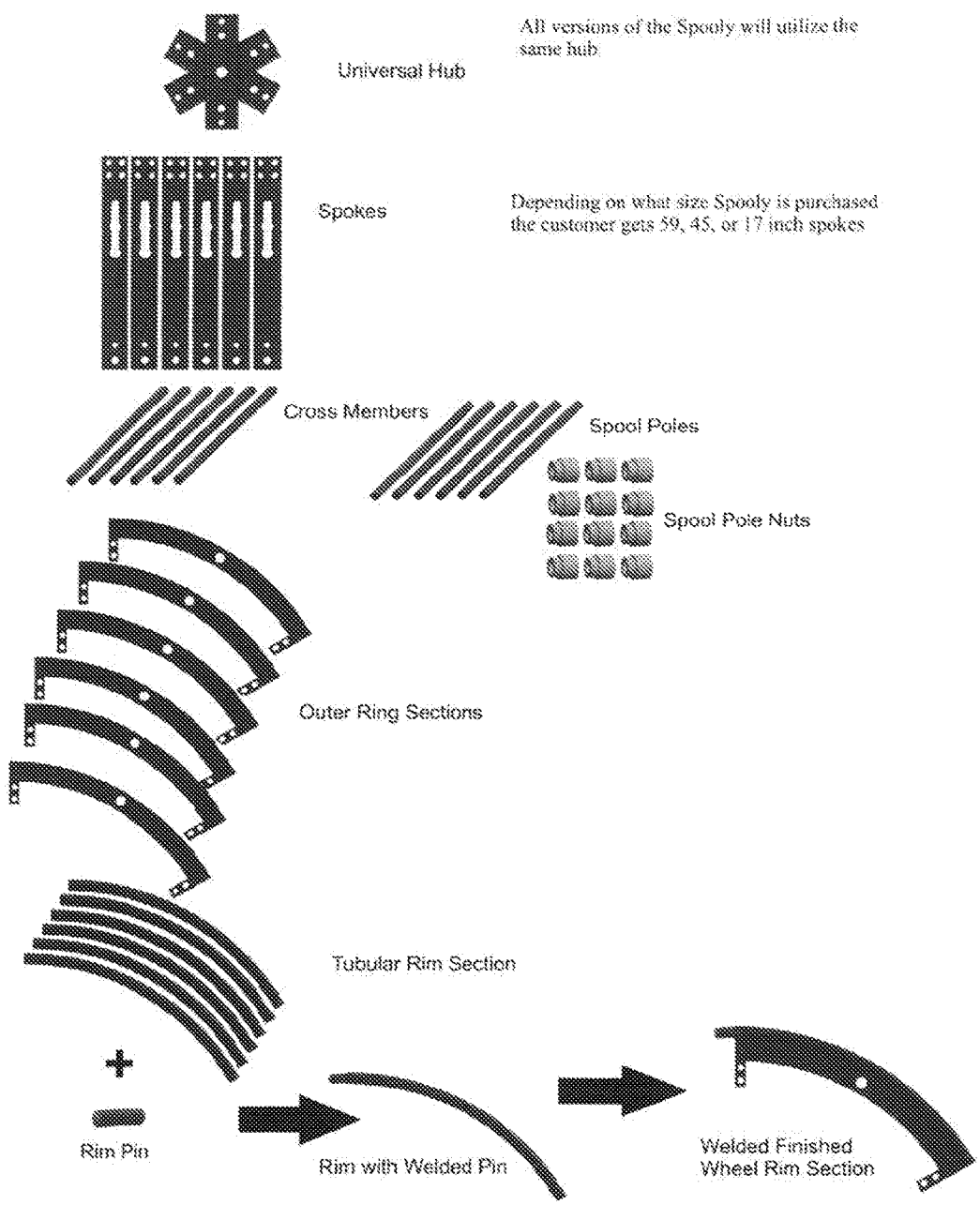
Figure 12C:
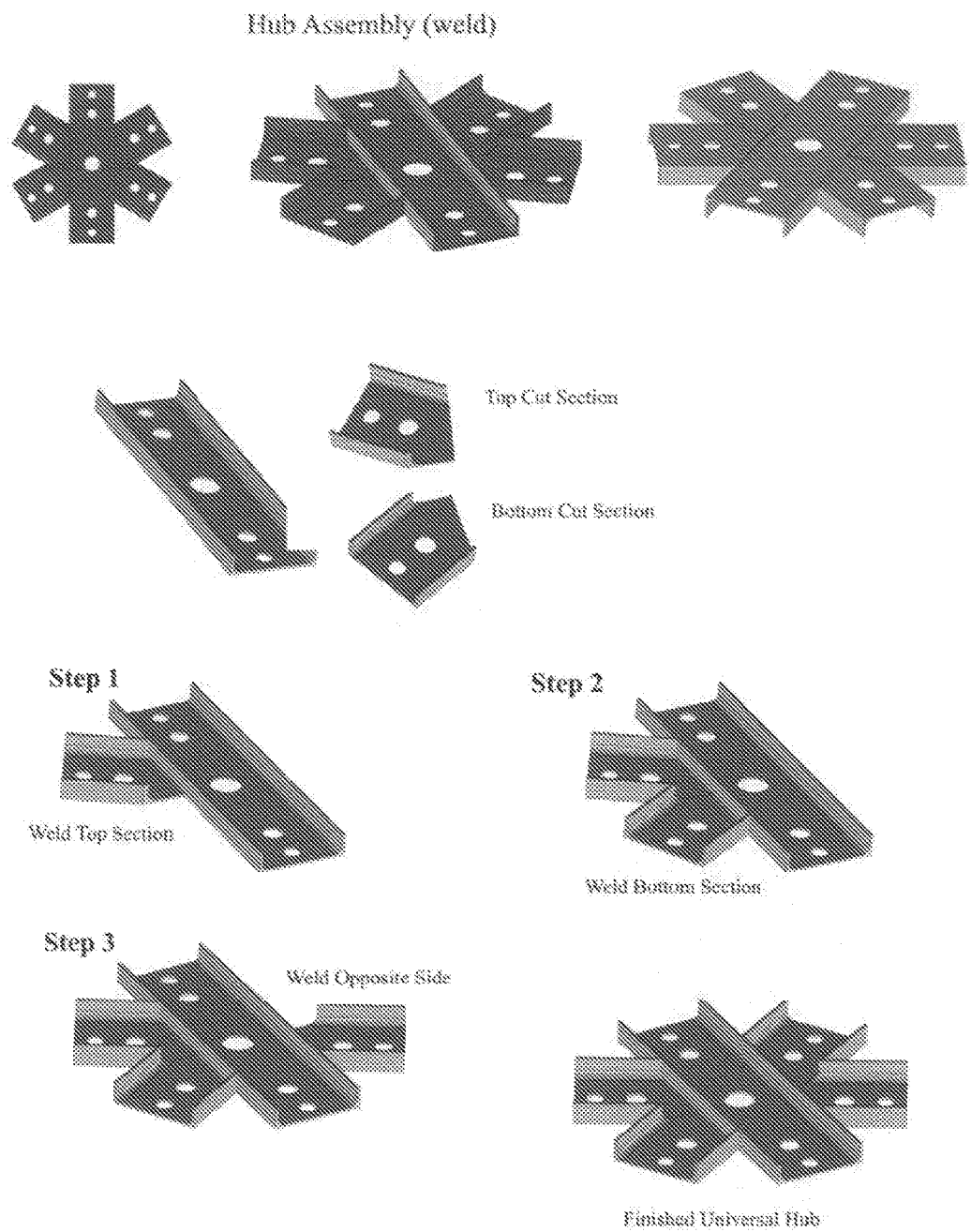
Figure 12D:
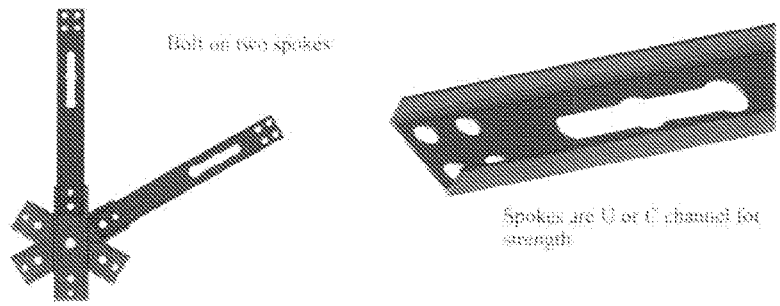
Figure 12E:
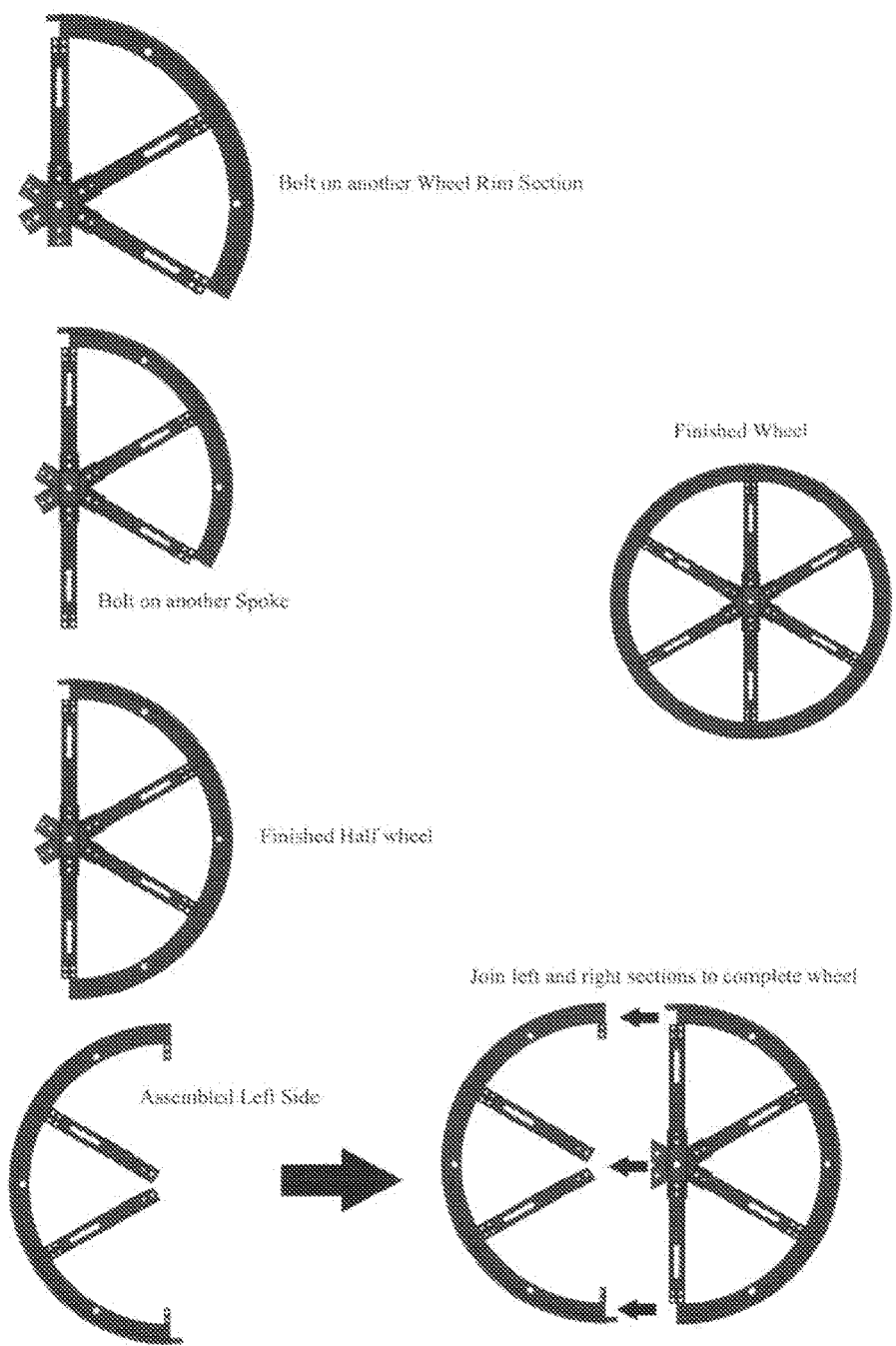
Figure 12F:
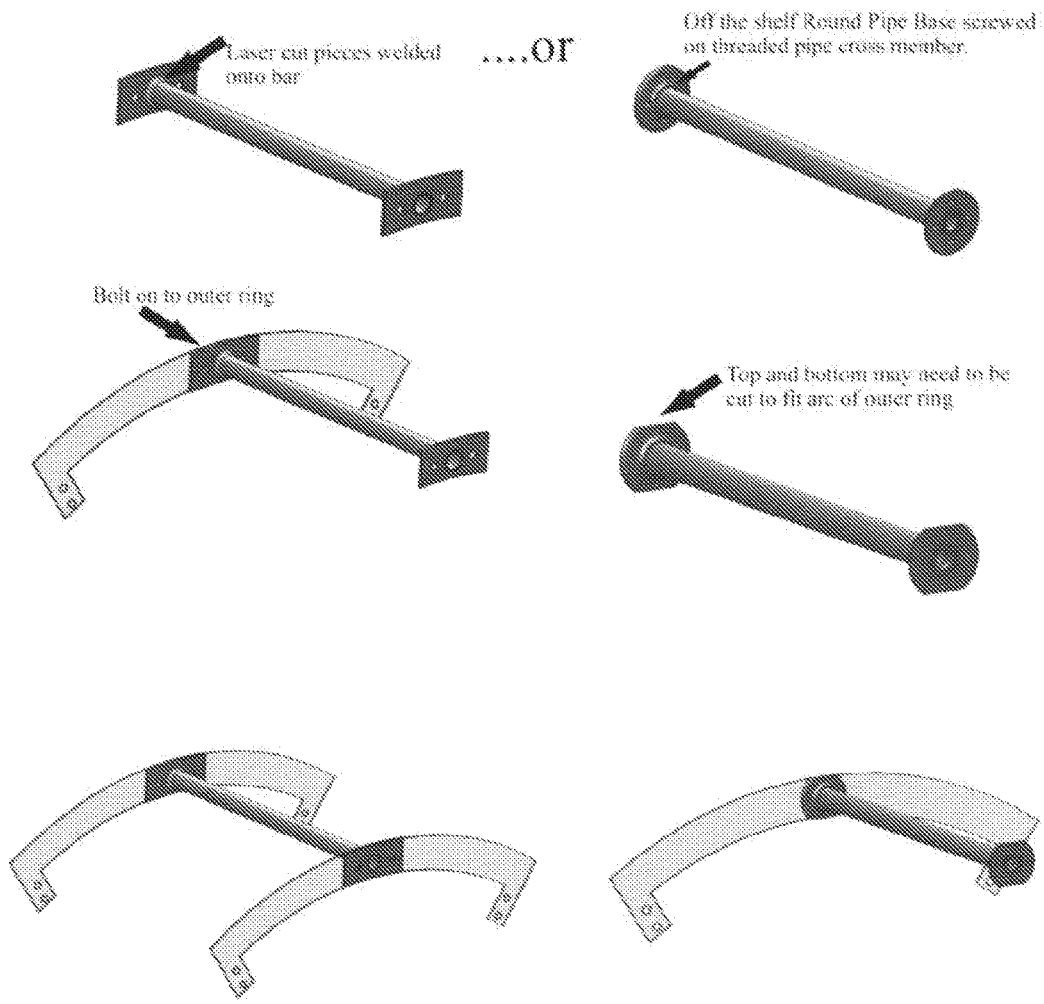
Figure 13:
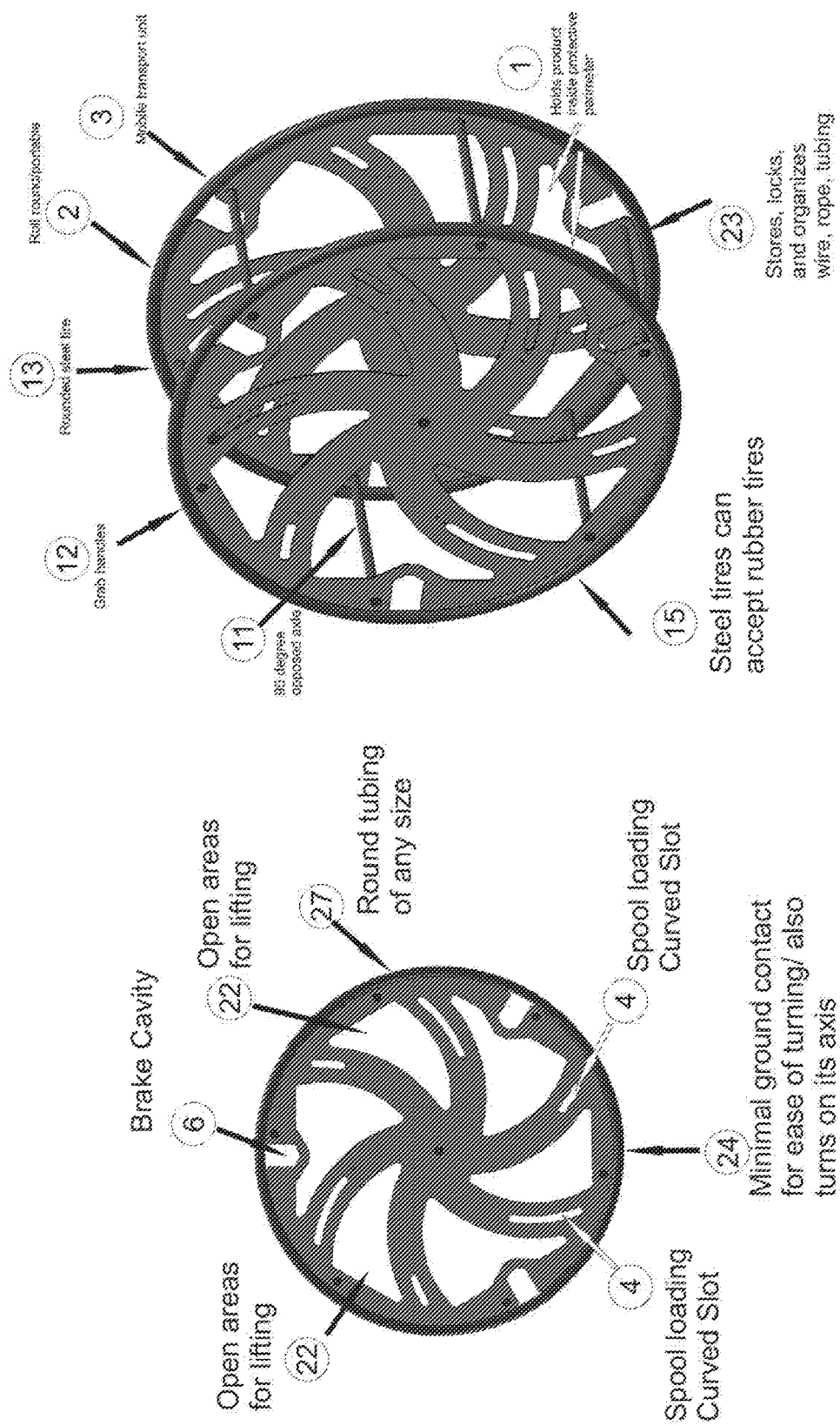
Figure 15:
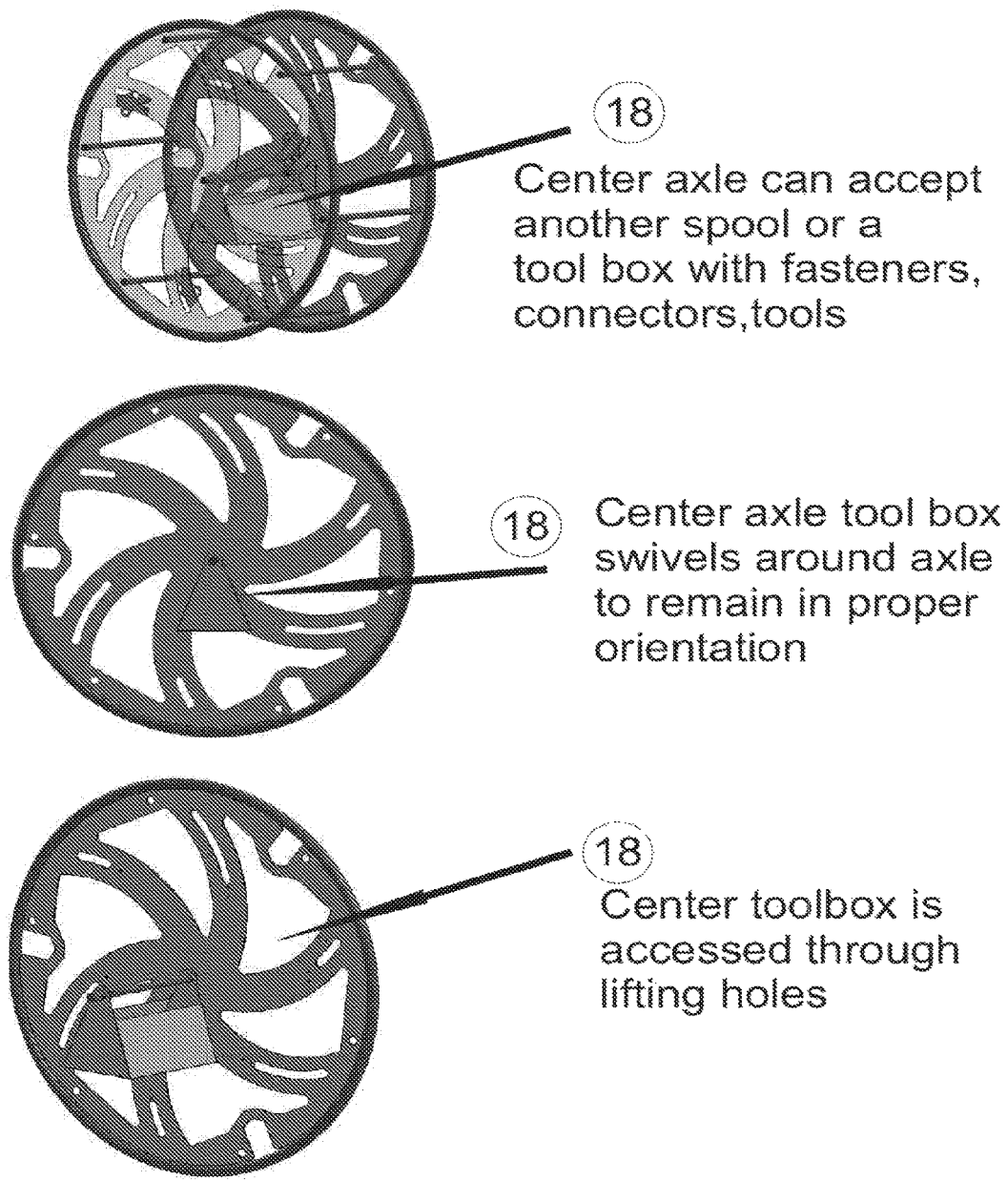
Figure 16:
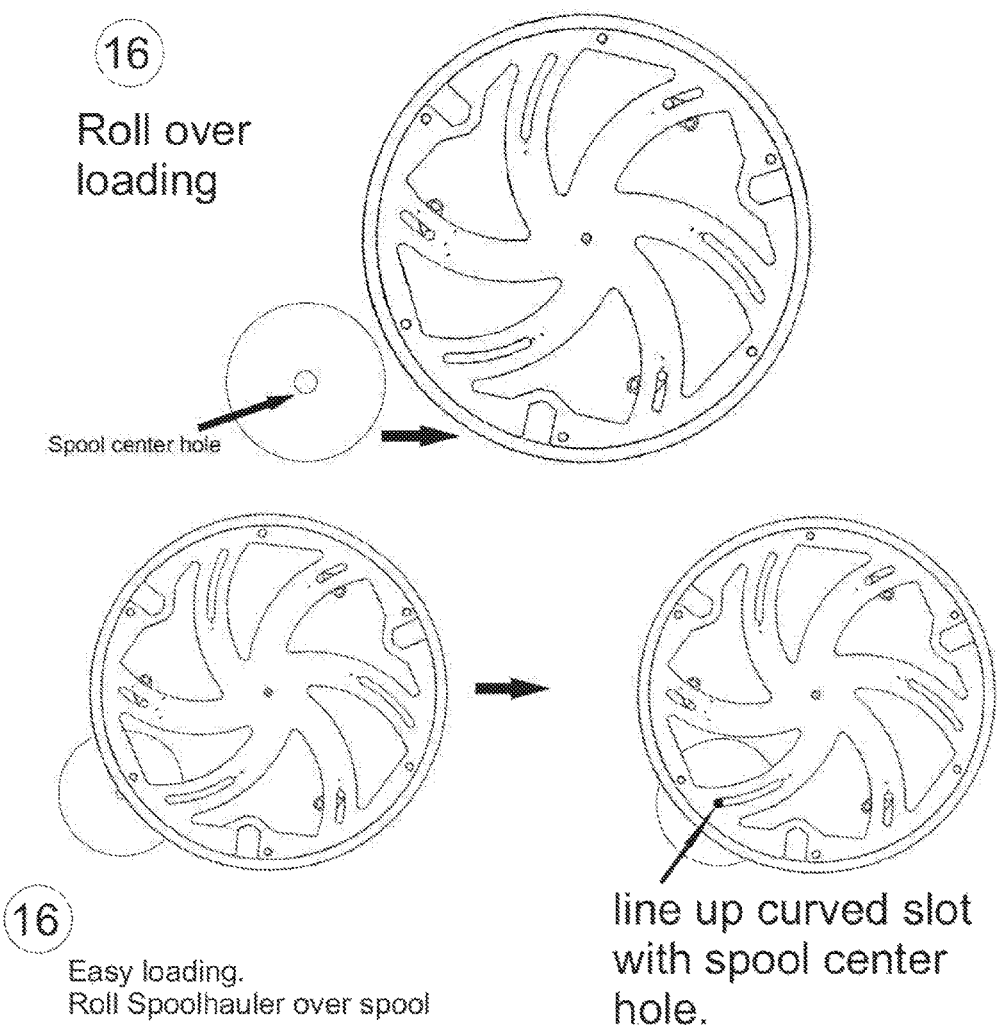
Figure 17:
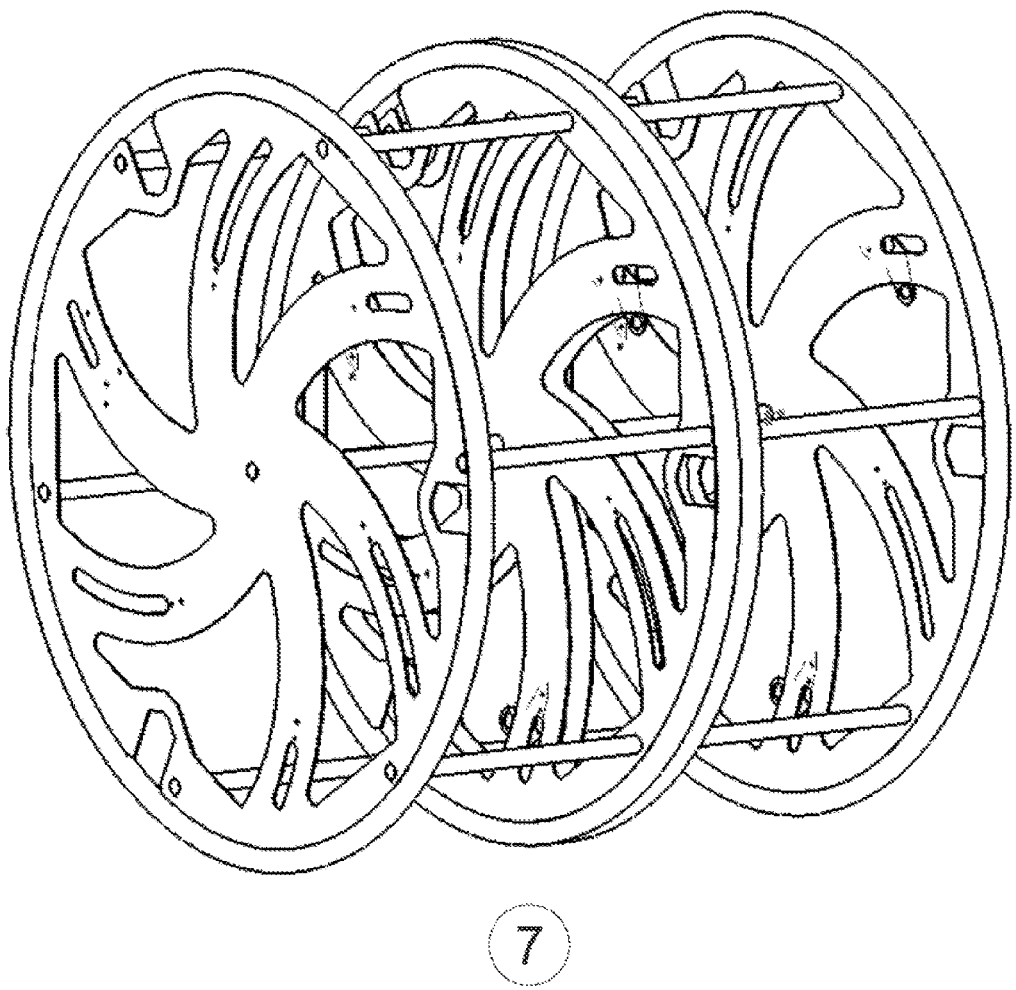
Figure 20:
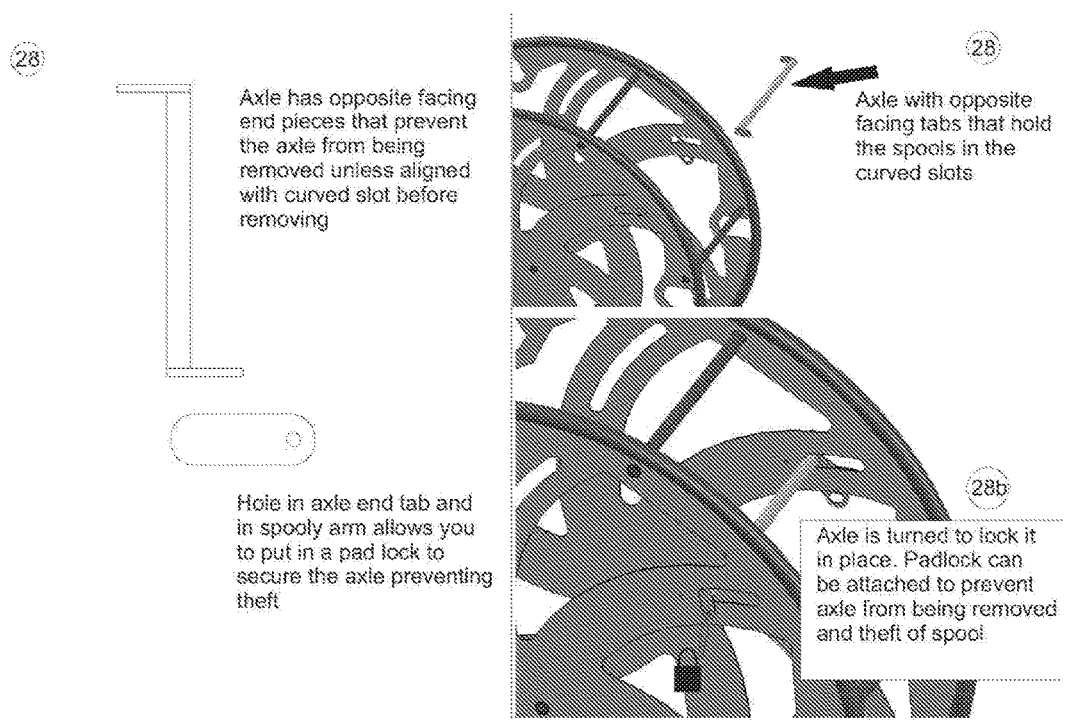

Referring now to FIG. 7, a 48-inch-diameter embodiment of a rolling spool rack 700 is seen in a side view, which shows only one platter 701-A of two identical, spaced-apart circular platters 701-A and 701-B (item number 701 applies to either). Each of the platters 701 is fabricated from a peripheral hoop 702, a central disc 703, and 5 plurality of radially-spaced spokes 704, which interconnect the central disc 703 to the peripheral hoop 702. The hoop 702 is constructed from a length of circularly-bent tubing, the ends of which are butt welded together, thereby forming the hoop 702. Each of the spokes 704 is constructed from a length of steel channel stock. The central disc 703 is, preferably, surrounded by a cylindrical wall 705, which is either formed with the disc 703 in a single stamping or welded to the periphery of the disc 703. The inner end 706 of each spoke 704 is welded to the cylindrical wall 705, with the spoke channels 707 and the cylindrical wall 705 on one side of the platter 701, which will be the outer side thereof. The outer end 708 of each spoke 704 is welded directly to the hoop 702, so that the flat major surface of each spoke (i.e., the surface behind the channel 707) is coplanar with the inner surface of the hoop 702. This configuration will enable spools of wire to be installed within the rolling spool rack without the hoop interfering with the entry thereof into the rack. An arcuate gusset 709 reinforces each section of hoop 702 between each pair of adjacent spokes 704, and is welded to the hoop 702, as well as to each of the adjacent spokes 704. Each spoke is 704 equipped 20 with a single axle aperture 710, as is the central disc 703. Each axle aperture 710 is reinforced with a surrounding flat washer 711 that is welded to the spoke 704. It should be noted that the positions of the hidden tubular cross braces are indicated by six broken-line circles 712-A, 712-B, 712-C, 712-D, 712-E and 712-F (item number 111 applies, generally, to any of the six tubular cross braces of the 48-inch-diameter embodiment of the rolling wire spool rack 700). The ends of each tubular cross brace 712 are welded to two opposing arcuate gussets 709 on opposite platters 701. Also shown in this side view of FIG. 7 is a configuration for the installation of 15.5-inch-diameter, 9.5-inch-wide spools (six are shown mounted on different, radially-spaced axles 713, and one is shown mounted on a central axle 714).

Referring now to this FIG. 8, the 48-inch-diameter embodiment of the rolling spool rack 700 is seen in a front or rear view, in which both platters 701-A and 701-Bare visible. The two platters 701-A and 701-B are held together by six tubular cross braces 711-A, 711-B, 711-C, 711-D, 711-E and 711-F. This particular embodiment has a width of 34 inches so that it can accommodate three 15.5-inch-diameter, 9.5-inch-wide spools in a side-by-side arrangement on a single axle. With three such spools on 5 seven axles, a total of twenty-one spools can be mounted on this 48-inch diameter embodiment of the rolling spool rack 700.

Referring now to FIG. 9, a 24-inch-diameter embodiment of a rolling spool rack 900 is seen in a side view, which shows only one platter 901-A of two identical, spaced-apart circular platters 901-A and 901-B (item number 901 applies to either). Each of the platters 901 is fabricated from a peripheral hoop 902 and a central patterned plate 903 cut from a single plate of steel stock. The central patterned plate 903 incorporates a central disc 904, a circular rim 905, and six equiangularly-spaced radial spokes 906, which interconnect the circular rim 905 to the central disc 904. The central patterned plate 903 is sized so that it can be welded to the hoop 902, with one major surface coplanar, or flush, with the inner surface thereof. It should be understood that although the platters of the larger diameter embodiments of the rolling wire spool rack 100, 500, and 700 can also be fabricated from a hope and a one-piece central patterned plate, the waste of steel is deemed excessive. In addition, for the larger diameter embodiments, the spokes fabricated from channel stock impart a desired degree of rigidity to the structure without a commensurate increase in rack weight. It should be clear that a one-piece central patterned plate, such as 903, can be cut with one of more saw tools, with laser cutter, with a high-pressure water cutter, or even milled, although laser or high-pressure water techniques are deemed to be the least expensive method. As with the other embodiments of the rolling spool rack 100, 500, and 700, the hoop 902 is constructed from a length of circularly-bent tubing, the ends of which are buttwelded together, thereby forming the hoop 902. This configuration will enable spools of wire to be installed within the rolling spool rack without the hoop interfering with the entry thereof into the rack. The circular rim 905 takes the places of the arcuate gussets of the other embodiments of the rolling wire spool rack 100, 500 and 700. Each spoke of the central patterned plate 903 is equipped with a single axle aperture 907-A. The central disc is also equipped with a single axle aperture 907-B. Each axle aperture 907 is reinforced with a surrounding flat washer 908 that is welded to its respective spoke 906. It should be noted that the positions of the hidden tubular cross braces are indicated by six broken-line circles 909-A, 909-B, 909-C, 909-D, 909-E and 909-F (item number 909 applies, generally, to any of the six tubular cross braces of the 24-inch-5 diameter embodiment of the rolling wire spool rack 900). The ends of each tubular cross brace 909 are welded to the two opposing circular rims 905 on opposite platters 901. Also shown in this side view of FIG. 9 is a configuration for the installation of showing a configuration for the installation of 7-inch-diameter, 5-inch-wide spools 910 (six are shown mounted on different, radially-spaced axles 911, and one is shown 10 mounted on a central axle 912).

Referring now to this FIG. 10, the 24-inch-diameter embodiment of the rolling spool rack 900 is seen in a front or rear view, in which both platters 901-A and 901-B are visible. The two platters 901-A and 901-B are held together by six tubular cross braces 908-A, 908-B, 908-C, 908-D, 908-E and 908-F. This particular embodiment has 15 a width of 23.5 inches so that it can accommodate four 7-inch-diameter, 5-inch-wide spools in a side-by-side arrangement on a single axle. With four such spools on seven axles, a total of twenty-eight spools can be mounted on this 24-inch diameter embodiment of the rolling spool rack 900.

Referring now to FIG. 11, a single representative spool axle assembly 1100 is shown, including a tubular axle 1101 threaded at both ends and a pair of retaining nuts 1102-A and 1102-B (1102, generally). As previously stated, the retaining nuts 1102 are fabricated by sawing a rigid electrical conduit couplings in half through its central axis. It should be understood that rigid electrical conduit and electrical couplings, unlike rigid water pipe and couplings therefor, have threads which are not tapered. Thus, the half-couplings function effectively as screw-on nuts. It should be understood that rigid pipe is, of course, available in different diameters, and that pipe of an appropriate diameter can be selected to accommodate spools having central aperture of a certain diameter. Likewise, rigid pipe or conduit of a desired diameter can be cut to appropriate lengths for any particular embodiment of the rolling wire spool rack. In addition, although all of the embodiments of the reliable wire dispensing spool racks are disclosed in widths that accommodate at least two spools on the same axle, other embodiments can be fabricated that accommodate fewer spools on a single axle by simply shortening each of the tubular cross braces. All other physical attributes of that particular embodiment of the rollable wire dispensing spool rack will remain the same.

FIGS. 12A-12F shows details for one rollable dispenser embodiment. Referring now to the drawing labeled "Spooly", this is an assembled knock-down or built-up embodiment of the Electrician's Rollable Wire Dispensing Spool Rack. Though the bolts and nuts holding the assembly together are not shown, it should be easily understood by someone having ordinary skill in the art that bolts and nuts can be used to secure the various components in a rigid integrated assembly. The knock¬ down design dramatically reduces shipping costs. The drawing labeled Universal Hub, Spokes, Cross Members, Spool Poles, Spool Pole Nuts, Outer Ring Sections, Tubular Rim Section Rim Pin, Rim with Welded Pin and Welded Finished Wheel Rim Section shows the various components required to make a single platter. The cross members, of course are used to interconnect both platters. The drawing labeled Hub Assembly (weld) shows the build-up of a hub from channel iron. It, of course, can be stamped from a single sheet of steel or stainless steel. The drawing labeled Wheel Assembly shows the attachment of a rim section with two spokes and the hub. Also shown in detail the slot detail of a single spoke. The drawings with the first drawing labeled Bolt on another Wheel Rim Section continues the assembly of the platter or wheel assembly. The wheel is constructed in two halves, which are then bolted together. The drawing labeled Loading the Spool shows how spools wound with wire are most easily loaded on the completed dispensing spool rack. The drawing labeled Cross Member shows two embodiments of bolt-on crossmembers. The spool rack could be built with more than two platters. However, two platter embodiments are considered the preferred embodiment. In the case of three platters, both platters would be spaced apart in a parallel, coaxial arrangement.

FIGS. 13-22 show another embodiment of the rollable dispenser. In this embodiment, a rollable dispenser for spooled wire looks much like a large hose reel except that the opposing plates on the dispenser are held together by equiangular-spaced tubular braces which rigidly interconnect the frames adjacent their circular peripheral edges. One or more wire spools are retained between the platters on removable axles which span the distance between both platters at radial intervals. One or more spools may also be retained by a centrally positioned axle. For a preferred embodiment of the invention, each platter is constructed from a length of circularly bent tubing, the ends of which are butt welded together to form a hoop. Each platter further includes a circular laminar plate that includes a circular rim, a central hub having a single axle aperture, and radial laminar spokes, each having an axle aperture, which join the rim to the hub.

For a preferred embodiment of the invention, the circular rim of the platter is constructed from a length of circularly-bent tubing, the ends of which are butt welded together to form a hoop. Each of the radial spokes is constructed from a length of steel channel stock. The central disc is surrounded by a cylindrical wall, which is either formed with the disc in a single stamping or welded to the periphery of the disc. The inner ends of the spokes are welded to the cylindrical wall, with the spoke channels and the wall of the central disc facing one direction, which will be the outer platter of the platter. The outer ends of the spokes are welded directly to the hoop so that the flat major surface of each spoke is coplanar with the inner surface of the hoop. This configuration will enable spools of wire to be installed within the rolling spool rack without the hoop interfering with the entry thereof into the rack. An arcuate gusset reinforces each section of hoop between each pair of adjacent spokes, and is welded to the hoop, as well as to each of the adjacent spokes. Each spoke is equipped with one or two axle apertures, which each axle aperture accommodating different spool sizes. Each axle aperture is reinforced with a surrounding flat washer that is welded to the spoke. For smaller-diameter embodiments of the invention, the entire central portion of the platter (i.e., spokes and central disc) can be stamped or cut from a single piece of steel plate stock. This can even be done for the larger-diameter embodiments, but with substantial waste of steel between the spokes.

Once a pair of platters has been fabricated, they are positioned parallel to one another, with the spokes and arcuate gussets of one platter radially aligned with the spokes and gussets, respectively, of the other platter. Each end of a tubular brace is then welded to a middle region of a gusset of each radially aligned pair of gussets, thereby interconnecting the platters, yet still leaving sufficient space to insert spools into the rollable rack from the periphery thereof. The tubular braces are radially spaced so that spools containing wound wire can be placed between the platters and mounted on a removable axle which spans the distance from one platter to the other. Each axle is preferably fabricated from a length of pipe that has been threaded on both ends. Retaining nuts are most easily made by sawing a pipe coupler in a direction that is perpendicular to the coupler's central axis.

The fabrication process results in a structure that can be easily rolled from one location to another, and which can be rolled up or down a loading ramp. The circular hoop on each platter serves several functions: it strengthens the outer edges of the platter, reduces rolling and turning friction, and minimizes the likelihood that the outer edges of the bobbin will cut items over which it might roll (e.g., worker's toes).

The rollable, spooled wire dispenser can be prevented from rolling by locking it in place with a chock modeled after those which have been used to chock airplane wheels for nearly a century. The rollable wire/cable dispenser can be manufactured in various diameters and in various widths to accommodate wire spools of different sizes and widths. Presently preferred embodiments of the invention are built with 60-inch, 48-inch, and 24-inch outplatter diameters. A 60-inch-diameter embodiment having a width of 37 inches can accommodate up to six 23.5-inch-diameter, 16-inch-wide spools (two spools on every other radially-spaced axle) wound with up to 2500 feet of #6 insulated wire and three 15.5-inch-diameter, 9.5-inch-wide spools (three spools on the central axle) wound with up to 1000 feet of #6 or #8 insulated wire. Alternatively, the 60-inch diameter embodiment can accommodate twenty-one 15.5-inch-diameter spools (three spools on each radially-spaced axle and three spools on the central axle) wound with up to 1000 feet of #6 or #8 insulated wire. A 48-inch-diameter embodiment having a width of 34 inches accommodates up to twenty-one 15.5-inch-diameter, 9.5-inch wide spools (three per axle) wound with up to 2500 feet of #10 or #12 insulated wire. A 24-inch-diameter embodiment having a width of 23.5 inches accommodates up to twenty-eight 7-inch-diameter, 5-inch-wide spools (two per axle) wound with up to 500 feet of #14 or #16 insulated wire.

With reference to FIGS. 13-22, the following items are shown and their functions are detailed below:

1. Holds Product Inside Perimeter
2. Roll Around Portable
3. Mobile Transport Unit
4. Spool Loading Curve Slot—Lifting Action—Straight S—Reduced Leverage For Ease Of Lifting
5. Special Lock—Holds Axle In Place
5.b Locked Position
5.c Pad Lock Design
6. Swing Out Brake—Stops Mobility
7. Double Up Side by Side To Increase Capacity
8. Obstacles—Designed to go over 2×4, 4×4, Cords, Conduit, Drywall
9. Construction Debris, Pallets
10. Difficult Terrain—Travels Over Snow, Grass, Sand, Gravel, Dirt easily
11. 90 degree Opposed Axle
12. Grab Handles
13. Rounded Steel Tire
14. Minimal Contact With Ground
15. Rubber Wheels or Other Non-Mar Material
16. Roll Over Loading
17. Designed to Fit Through Interior Doors
18. Center Accessories Bin Tool Box: Materials of Construction—Wood, Steel, Aluminum, Stainless Steel, Composite, Molded (Drawing)
19. Blank
20. Techniques—Standing—Not Bending, Stand Up Loading—To be described
21. Use With—Wire, Rope, Tubing
22. Openings To Be Used For—Lifting, Hoisting, Crane, Via Chain, Rope, Block & Tackle
23. Storage Locker—Organizes, Wire, Rope, Tubing, Tools, Connections, Stores, Locks (Drawing)
24. Minimal Ground Contact—Turn On It's Own Axis, Rapid Turns, Tricky Hallways, Narrow Spaces
25. Multiple Sizes—Small, Medium, Large, DoubleSize
26. Auto Brake—Wrist band hooked to pin, if pulled out, brake engages
27. Use Any size tubing for wheel
28. Axle Design
29. Curved Slots for Easy Loading Referencing the above numbers:

1) The spools of wire are held inside the two disks that form the Dispenser. These spools are held 2 to 6 inches off the ground and hence away from the outer round tubular tire area and hence away from the operators hands as he rolls the dispenser.

2) One of the dispenser's functions is an onsite rollable storage unit for wire, rope, tubing, and string. It can be moved by simple rolling its entire body from place to place since the wire, rope or tubing is stored within the body of the device.

3) The Dispenser is mobile and can be moved by truck or transport either empty or with the wire or tubing loaded into it.

4) The slots in the curved arms are one of the main features that make the dispenser viable as a solution to moving wire, tubing or rope spools. Larger wire spools can weigh 600-800 pounds. In order for the Dispenser to work properly these spools must be stored inside the Dispenser and some 2-6 inches off the ground.

As the operator is unlikely to lift these spools even two inches off the ground means the a solution needed to be found. If there was simple a hole in the curved arms of the dispenser the spools could be attached but not held away from the floor. This would mean the spools would hit the ground with each rotation. Each spool needs to be away from the edge and this is accomplished by having a slot in the curved arms. The operator positions the spool of wire and then rolls the Dispenser over the spool and lines up the slot with the hole in the center of the spool. (point 16)

When the hole in the spool is lined up with the slot then the operator inserts a metal axle (point 28) through the slot passing it though the spool and out the other side through the other slot. This captures the spool with the axle. The operator now rolls the Dispenser back allowing the axle and spool to slide along the slot towards the center of the Dispenser. When it nears the end of the slot the axle is captured by a locking mechanism which holds it in place until the operator opens the lock and lets the axle and spool slid down the other end of the slot near the edge of the Dispenser. Removal of the axle disconnects the spool from the Dispenser.

A curved slot (point 4) is used because it gives a better leverage advantage and is a more gradual slide for the axle for loading and unloading. The curve also means that you don't have to roll the Dispenser back as far to get the axle to roll towards the center of the Dispenser as you would with a straight slot. (point 29)

(5) The lock is also a major feature that makes the Dispenser work where other designs fail. When the axle has been inserted thru the slot and spool and thru the opposite side slot the spool is still in contact with the ground. The axle is also free to move freely along the slots path. When the Dispenser is rolled either forward or backwards at some point the slot moves away from the ground on its way to being perpendicular to the ground and in so doing lifts the spool off the surface its resting on. As the slots moves up and around the axle due to gravity will eventually slide down the slot towards the center of the dispenser. At about 2 inches from the end of the slot closest to the center of the Dispenser a mechanical lock is located. This lock is spring loaded so as to be always closed. The lock consists of a spring, a hook, a support plate, a lock pin and five mounting bolts. The hook has a circular cut out in it that corresponds to the diameter of the axle. This circular cutout also corresponds to the circular diameter at the end of the slot. The hook also has on one end an angled face and on the other end a tapered point. The hook also has an oversized oblonged hole towards the tapered point where a bolt passes thru and attaches the hook to the lock assembly. The bolt has a standoff so it is tightened to hold the hook on but allows the hook to remain loose enough to swivel. The closed position of the lock means that the hook is down and covering or blocking the path of the slot. The tension of the spring keeps the hook in this "closed" position covering the slot. The front of the hook has an angle on it and this angle faces the approaching axle. When the axle comes in contact with the hook the angle on the hook is pushed back by the roundness of the axle lifting the hook up and out of the way of the advancing axle. When the axle reaches the end of the slot the circular cutout in the hook lets the hook drop back down and around the axle capturing it. The spring tension holds the hook down preventing the axle and hence the spool from moving back down the slot.

(5a) When one wants to remove a spool from the Dispenser the Dispenser is rolled so as to position the spool up at the 12:00 o'clock position. This takes the weight off the lock hook. With the weight off the operator puts his finger thru the large hole in the hook and pulls the hook backwards or away from the axle. The hook is held onto the lock assembly by a single large bolt that the hook swivels around. When the operator pulls the hook backwards the bottom or tapered end comes in contact with the lock pin. When the operator exerts more pressure the hook lifts up sliding along the oblonged hole allowing the tapered point to slip up and over the lock pin. As a result of the spring tension the hook is now pulled downward and is captured by the lock pin. This capturing prevents the hook from returning to its locked or closed position in effect rendering it "open". The operator now opens the lock just opposite so that the two locks that hold common single axle both reside in the open position.

(5b) The operator now rolls the Dispenser forward or backwards and when doing so the axle will gently slide back down the slot towards the floor. When the spool is in full contact with the floor the operator removes the axle and rolls the Dispenser away leaving the spool on the ground.

(5c) With hook in closed position securing the axle a padlock is able to be put thru corresponding holes to secure hook in locking mechanism so hook cannot be lifted and axle and spool removed. Theft protection.

(6) The brake consists of a rotating block that stores inside a cavity on the large disks that make up the wheels of the Dispenser. When the Dispenser reaches its destination the operator uses either his hand or foot to rotate the block 180 degrees inline with the wheel and facing the floor. When the job is completed the operator rotates the block back 180 degrees to its storage position and is now free to roll the Dispenser away.

(7) Two or more Dispensers can be daisy chained together for greater storage and job efficiency.

(8) (9) (10) Because of the diameter of the Dispenser wheels the physics allows the operator to roll over most common construction debris that completely stops every other wire cart in use today. This same advantage allows the Dispenser to be taken thru grass, sand, dirt, and snow without clogging & with minimal effort.

(11) Most wire carts in use today use axles or poles that are at lifted angles to prevent the spool from falling off. Dispenser uses 90 perpendicular axle configuration to give the smoothest most efficient delivery of wire

(12) The design of the outer tires is accomplished by rolling a round tube into a circle and then butt welding to form a continuous ring. This smooth surface also provides the gripping, turning, and maneuvering handles for the moving of the Dispenser.

(13) The use of rounded tubular steel rolled into a continuous circle means that there are no sharp or angular surfaces to cut or mar floors

(14) By utilizing a round circular tube to form the wheels of the Dispenser there is minimal contact with the ground. (24) That low surface contact means that the rolling and turning resistance is very low. This allows the Dispenser to easily be turned laterally 360 degrees within its own footprint.

(15) The rounded tubular wheels allows us to put a rubber shoe or sheath onto the wheels to further protect the floor

(17) The Dispenser is designed for maximum spool size used in residential and commercial buildings while still maintaining its ability to pass thru interior doorways.

(18) When the center axle is not needed for a spool of wire a tool bin that is so designed that it hangs below the centerline and so that it never rotates can be attached. This bin holds all the tools, fasteners and necessities for the job.

(20) Because the Dispenser can be rolled this means that the wire spools can be positioned in such a way as to relief stress on the operator by adjusting the height of the spools that is most comfortable for him to work.

(21) Dispenser holds and dispenses wire, rope, chain, tubing, any spooled medium

(22) The triangular openings on the side of the Dispenser wheels allows the operator access into the interior of the dispenser and the spools in case of tangles etc. These openings also allow a pole or chain or cable to be passed thru enabling the Dispenser to be lifted into a truck or to elevated floors.

(23) Instead of having spools laying around a shop or warehouse the Dispenser can be used as an organizer and storage device for unused inventory (23b) The dispenser can be offered preloaded with the required spools length and diameter of wire or product.

(25) The dispenser can come in various sizes depending on the job requirement.

(26) Auto Braking. Braking mechanism can be setup to include a tethered device that automatically engages an electronic brake that deploys immediately upon separation from operators control.

(27) Wheels, disks, axles, spars, openings, slots, metal thickness, diameters, widths can be used to meet needs of various job, weight, location specifications.

(28) The axle that passes thru the slot and spool hole and out the other side slot has a unique end-cap. At each end of the axle there are oval metal tabs welded so that the tab of the one side faces in opposite direction as the tab of the other side. On the non welded side of each tab a hole is drilled that corresponds to a hole in the disks of the Dispenser. When loading the Dispenser and inserting the axle into the slot the oval tab is aligned so that it can pass thru the slot. After passing thru the spool it must be aligned again to pass out the other slot on the opposite side. Once thru the slot the axle is turn such that the tab is now not aligned with the slot and therefore cannot be pulled back thru the slot. Also, the slot on the other end cannot be pushed thru the slot. To remove the axle the operator has to once again turn the axle so that the tab aligns with the slot and can be pulled out.

(28b) The small hole at the non welded end of the tab that corresponds to a hole in the disk of the Dispenser allows a padlock to be placed thru it to prevent theft Although only several embodiments of a rolling wire spool rack have been shown and described, it will be obvious to those having ordinary skill in the art that changes and modifications may be made thereto without departing from the scope and the spirit of the invention as may be hereinafter claimed.

What is claimed is:

1. A rollable dispenser, comprising:
    first and second circular platters to roll on a ground;
    a plurality of equiangular-spaced tubular braces which rigidly interconnect the frames adjacent their circular peripheral edges;
    one or more spools retained between the first and second platters on removable axles spanning both platters at radial intervals, wherein the spools are loaded as the platters are rolled and wherein the platter comprises one or more brake cavities enclosing a brake in the platter when inactive, wherein the brake swings out of the platter when deployed.

2. The dispenser of claim 1, wherein the one or more wire spools are retained by a centrally positioned axle.

3. The dispenser of claim 1, wherein each platter is constructed from a length of circularly bent tubing and wherein the tubing ends are butt welded together to form a hoop.

4. The dispenser of claim 1, wherein each platter is constructed from rounded steel tire that accepts a rubber tire.

5. The dispenser of claim 1, wherein the platter comprises curved spokes with open areas in between for lifting or access.

6. The dispenser of claim 1, comprising a center axle to accept a spool or a tool box, wherein the spool or tool box swivels around the axle when the dispenser is rolled.

7. The dispenser of claim 6, wherein the tool box is accessed through lifting holes on the platter.

8. The dispenser of claim 1, wherein the platter receives a spool using a roll over loading where a spool center hole is aligned with a curved slot on the platter and the dispenser is rolled over the spool to load the spool.

9. The dispenser of claim 1, comprising a second dispenser placed adjacent to one of the platters and secured using axles extending through both dispensers.

10. The dispenser of claim 1, wherein the platters are spaced apart with a width that fits door width or hallway width or passageway width.

11. The dispenser of claim 1, comprising a lock to hold an axle in place, wherein the lock has a slot at a same level as a spool center hole to insert the axle in the slot and through a spool, wherein when the dispenser is rolled the axle with the spool rolls back towards an opposite end of the slot to be automatically secured by the lock.

12. The dispenser of claim 1, comprising an axle with opposite facing end pieces that prevent removal of the axle unless aligned with a curved slot prior to removal.

13. The dispenser of claim 12, comprising an opening in the axle to receive a padlock arm to secure the axle with a spool mounted thereon.

14. The dispenser of claim 1, wherein the platter comprises one or more spool loading curved slot to receive a spool while the dispenser rolls.

15. The dispenser of claim 1, wherein each platter further includes a circular laminar plate that includes a circular rim, a central hub having a single axle aperture, and radial laminar spokes, each having an axle aperture to join the rim to the hub.

16. The dispenser of claim 1, comprising:
elongate cross braces are metal pipe, with a first end of each being right-hand threaded and a second end being left-hand threaded;
one platter is fitted with a set of right-hand threaded couplings, the other platter is fitted with a set of left-hand threaded couplings;
said sets of couplings are secured to an inner surface of their respective platter at radially-spaced locations adjacent a periphery thereof; and
said platters are joined together by rotatably and simultaneously engaging one right-handed coupling and one left-handed coupling with each elongate cross brace.

17. The dispenser of claim 1, comprising multiple spokes of each platter each equipped with a radially-disposed slot having a plurality of axle securing means at different radial distances from the central axis, wherein each of said axles is a section of pipe threaded at both ends thereof and a securing device with:
multiple semi-circular cutout pairs on opposite sides of each slot, each semi-circular cutout being spaced from other semi-circular cutout pairs along the same slot, each semi-circular cutout pair providing an axle securing location within that slot; and
a securing nut for each end of said pipe-section axles, each securing nut having a stepped shoulder sized to engage one semi-circular cutout pair in a slot.

18. The dispenser of claim 1, wherein each of said platters is a built-up assembly comprising:
a central hub;
five or more spokes;
a plurality of identical platter rim sections, each of which comprises an arcuate plate member, a tubular rim member welded to the arcuate plate member, and an alignment pin protruding from one end of the tubular rim member; and
wherein said central hub, each of said spokes and each platter rim section is equipped with bolt holes that enable one end of each spoke to be bolted to the hub in an equally-spaced radial pattern, and the opposite end of each spoke to be bolted to an abutting pair of platter rim sections, thereby securing together each abutting platter rim section pair.

19. An electrician's dispenser for insulated metal wire conductors wound on spools, comprising:
at least two parallel, coaxial, spaced-apart, generally circular platters adapted to be rolled on a surface for loading spools and for ambulation of the spools to a selected location, each platter having a generally circular rim and a framework connecting the circular rim to a central hub, the platters secured to each other by equiangularly-spaced tubular braces which rigidly interconnect the platters near their peripheral edges;
a plurality of axles, each of which is removably installable between said platters at fixed locations that are either parallel or coincident with a central axis of the dispenser, which passes through a center of each hub, each of said axles intended to carry at least one conductor-wound spool, wherein said framework consists of equiangularly-spaced spokes, which emanate from the hub and connect to the circular rim; and
one or more spools retained by an axle passing through the platter's central axis, wherein the spools are loaded as the platters are rolled and wherein the platter comprises one or more brake cavities enclosing a brake in the platter when inactive, wherein the brake swings out of the platter when deployed.

* * * * *